(12) United States Patent
Chiamvimonvat et al.

(10) Patent No.: US 10,369,141 B2
(45) Date of Patent: Aug. 6, 2019

(54) METHODS OF IMPROVING CELL-BASED THERAPY

(71) Applicant: The Regents of the University of California, Oakland, CA (US)

(72) Inventors: Nipavan Chiamvimonvat, Davis, CA (US); Bruce D. Hammock, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/915,637

(22) Filed: Mar. 8, 2018

(65) Prior Publication Data
US 2018/0200244 A1 Jul. 19, 2018

Related U.S. Application Data

(63) Continuation of application No. 14/737,263, filed on Jun. 11, 2015, now abandoned.

(60) Provisional application No. 62/012,422, filed on Jun. 16, 2014.

(51) Int. Cl.

| | | |
|---|---|---|
| *A01N 63/00* | (2006.01) | |
| *A01N 65/00* | (2009.01) | |
| *A61K 31/4468* | (2006.01) | |
| *A61K 35/545* | (2015.01) | |
| *A61K 31/195* | (2006.01) | |
| *A61K 31/336* | (2006.01) | |
| *A61K 35/34* | (2015.01) | |
| *A61L 31/00* | (2006.01) | |
| *A61L 31/16* | (2006.01) | |
| *A61K 9/70* | (2006.01) | |
| *A61K 35/28* | (2015.01) | |
| *A61K 31/17* | (2006.01) | |
| *A61K 31/197* | (2006.01) | |
| *A61K 31/22* | (2006.01) | |
| *A61K 31/415* | (2006.01) | |
| *A61K 31/4465* | (2006.01) | |

(52) U.S. Cl.
CPC ........ *A61K 31/4468* (2013.01); *A61K 9/7023* (2013.01); *A61K 31/17* (2013.01); *A61K 31/195* (2013.01); *A61K 31/197* (2013.01); *A61K 31/22* (2013.01); *A61K 31/336* (2013.01); *A61K 31/415* (2013.01); *A61K 31/4465* (2013.01); *A61K 35/28* (2013.01); *A61K 35/34* (2013.01); *A61K 35/545* (2013.01); *A61L 31/005* (2013.01); *A61L 31/16* (2013.01); *A61L 2300/432* (2013.01); *A61L 2300/64* (2013.01); *A61L 2430/20* (2013.01)

(58) Field of Classification Search
CPC .. A61K 31/4468; A61K 9/7023; A61K 35/34; A61L 31/16

USPC ....................................................... 424/93.71
See application file for complete search history.

(56) References Cited

U.S. PATENT DOCUMENTS

| | | |
|---|---|---|
| 5,955,496 A | 9/1999 | Hammock et al. |
| 6,531,506 B1 | 3/2003 | Kroetz et al. |
| 6,831,082 B2 | 12/2004 | Ingraham et al. |
| 8,242,170 B2 | 8/2012 | Chiamvimonvat et al. |
| 2002/0077355 A1 | 6/2002 | Liao et al. |
| 2002/0165183 A1 | 11/2002 | Herweijer et al. |
| 2003/0023130 A1 | 1/2003 | Ciaccio et al. |
| 2003/0139469 A1 | 7/2003 | Weiss et al. |
| 2003/0144198 A1 | 7/2003 | Collins |
| 2004/0092567 A1 | 5/2004 | Ingraham et al. |
| 2004/0126879 A1 | 7/2004 | Schneider et al. |
| 2005/0164951 A1 | 7/2005 | Hammock et al. |
| 2005/0222252 A1 | 10/2005 | Hammock et al. |
| 2005/0288331 A1 | 12/2005 | Bush et al. |
| 2009/0216318 A1 | 8/2009 | Chiamvimonvat et al. |
| 2016/0008342 A1 | 1/2016 | Chiamvimonvat et al. |

FOREIGN PATENT DOCUMENTS

| | | |
|---|---|---|
| WO | WO 00/23060 A2 | 4/2000 |
| WO | WO 2006/045119 A2 | 4/2006 |
| WO | WO 2006/133257 A2 | 12/2006 |

OTHER PUBLICATIONS

Kawamura (2012, Circulation, 126(Suppl 1) S29-S37).*
Ingraham (2011, Current Medicinal Chemistry, 18:587-603).*
U.S. Requirement for Restriction/Election dated Mar. 28, 2011 issued in U.S. Appl. No. 11/921,676.
U.S. Office Action dated Jul. 12, 2011 issued in U.S. Appl. No. 11/921,676.
U.S. Final Office Action dated Feb. 3, 2012 issued in U.S. Appl. No. 11/921,676.
U.S. Notice of Allowance dated May 3, 2012 issued in U.S. Appl. No. 11/921,676.
U.S. Requirement for Restriction/Election dated Oct. 21, 2016 issued in U.S. Appl. No. 14/737,263.
U.S. Office Action dated Apr. 17, 2017 issued in U.S. Appl. No. 14/737,263.

(Continued)

*Primary Examiner* — Valarie E Bertoglio
(74) *Attorney, Agent, or Firm* — Mintz Levin Cohn Ferris Glovsky and Popeo, P.C.

(57) ABSTRACT

Provided are methods for improving cell-based therapies by co-administration with an agent that increases the production and or levels of epoxygenated fatty acids, as well as kits, stents and patches for co-administering stem cells with an agent that increases the production and/or levels of epoxygenated fatty acids.

21 Claims, 18 Drawing Sheets
Specification includes a Sequence Listing.

(56) References Cited

OTHER PUBLICATIONS

U.S. Final Office Action dated Dec. 19, 2017 issued in U.S. Appl. No. 14/737,263.
PCT International Search Report dated Oct. 16, 2007 issued in Application No. PCT/US06/22054.
PCT International Preliminary Report on Patentability and Written Opinion dated Dec. 6, 2007 issued in Application No. PCT/US06/22054.
European Search Report dated Jul. 16, 2009 issued in Application No. EP 06 772 386.6.
European Office Action dated Jan. 3, 2011 issued in Application No. EP 06 772 386.6.
European Intention to Grant dated Jun. 5, 2012 issued in Application No. EP 06 772 386.6, 60 pp.
European Decision to Grant dated Oct. 18, 2012 issued in Application No. EP 06 772 386.6, 2pp.
European Notice of Opposition dated Nov. 14, 2012 issued in Application No. EP 06 772 386.6, 6pp.
European Opposition Statement dated Aug. 9, 2013 issued in Application No. EP 06 772 386.6, 58pp.
European Communication of notices of opposition (R. 79(1) EPC) dated Sep. 19, 2013 issued in Application No. EP 06 772 386.6, 1page.
European Summons to attend oral proceedings pursuant to Rule 115(1) EPC dated Jan. 7, 2015 issued in Application No. EP 06 772 386.6, 9pp.
European Written Submissions in preparation to Oral Proceedings dated Jun. 12, 2015 issued in Application No. EP 06 772 386.6, 8pp.
European Withdrawal from Oral Proceedings dated Jun. 26, 2015 issued in Application No. EP 06 772 386.6, 10pp.
European Decision of Opposition dated Aug. 3, 2015 issued in Application No. EP 06 772 386.6, 13pp.
European Notice of Appeal dated Oct. 5, 2015 issued in Application No. EP 06 772 386.6, 6pp.
European Grounds of Appeal dated Oct. 13, 2015 issued in Application No. EP 06 772 386.6, 9pp.
European Statement of Grounds of Appeal dated Dec. 3, 2015 issued in Application No. EP 06 772 386.6, 17pp.
Ai et al., (2008) "Soluble epoxide hydrolase plays an essential role in angiotensis II-induced cardiac hypertrophy," *Proc. Natl. Acad. Sci., Early Edition*, 6 pages.
Bolli et al., (Nov. 26, 2011) "Cardiac stem cells in patients with ischaemic cardiomyopathy (SCIPIO): initial results of a randomised phase 1 trial," *The Lancet*, 378:1847-1857. [electronically published on Nov. 14, 2011].
Deng et al., (Dec. 2015) "Aerobic exercise-based rehabilitation affects the activities of progenitor endothelial cells through EETs pathway," *Med Hypotheses*, 85(6):1037-1038.
Fang et al., (Mar. 2005) "Activation of Peroxisome Proliferator-Activated Receptor α by Substituted Urea-Derived Soluble Epoxide Hydrolase Inhibitors," *The Journal of Pharmacology and Experimental Therapeutics*, 314(1):260-271. [Published-Evidence-1] [EP 06 772 386].
Fang et al., (May 2001) "Pathways of Epoxyeicosatrienoic Acid Metabolism in Endothelial Cells: Implicatiin for the Vascular Effects of Soluble Epoxide Hydrolase Inhibitors," *The Journal of Biological Chemistry*, 276(18):14867-14874.
Foley et al., (1996) "Impact of hypertension on cardiomayopathy, morbidity and mortality in end-stage renal disease" *in Kidney International*, 49:1379-1385.
Hong et al., (2014) "Cardiac Stem Cell Therapy for Cardiac Repair," *Curr Treat Options Cardio Med*, 16:324, 19pp.
Irukayama-Tomobe, (Feb. 2004) "Endothelin-1-Induced Cardiac Hypertrophy Is Inhibited by Activation of Peroxisome Proliferator-Activated Receptor-alpha Partly Via Blockade of c-Jun $NH_2$-Terminal Kinase Pathway," *Circulation*, 109:904-910. [Published-Evidence-2] [EP 06 772 386].
Irukayama-Tomobe, (Nov. 2004) "Activation of Peroxisome Proliferator-activated Receptor-alpha Decreases Endothelin-1-induced p38 Mitogen-activated Protein Kinase Activation in Cardiomyociytes," *J Cardiovasc Pharmacal*,44(Supplement 1):S358-S361. [Published-Evidence-4] [EP 06 772 386].
International Society for Stem Cell Research, ISSCR, 12th Annual Meeting, Vancouver, Canada, Jun. 18-21, 2014, "Poster Abstracts," 4pp.
International Society for Stem Cell Research, ISSCR, 12th Annual Meeting, Vancouver, Canada, Jun. 18-21, 2014, ISSCR-Poster, Final, 1 page: Sirish et al. "Soluble Epoxide Hydrolase Inhibitors in Cell-Based Therapy for Myocardial Infarction."
Karara et al., (Nov. 1989) "Endogenous Epoxyeicosatrienoic Acids: Cytochrom P-450 Controlled Stereoselectivity of the Hepatic Arachidonic Acid Epoxygenase," *The Journal of Biological Chemistry*, 264(33):19822-19827.
Lalit et al., (Apr. 11, 2014) "Induced Pluripotent Stem Cells for Post-Myocardial Infarction Repair: Remarkable Opportunities and Challenges," *Circ Res.*, 114:1328-1345.
Lee et al., (Aug. 15, 1999) "Effects of epoxyeicosatrienic acids on the cardiac sodium channels in isolated rat ventricular myocytes," *The Journal of Physiology*, 519(1):153-168.
Lian et al., (2012) "Robust cardiomyocyte differentiation from human pluripotent stem cells via temporal modulation of canonical Wnt signaling," *Proc. Natl. Acad. Sci.*, E1848-E1857.
Lieu, (Feb. 2013) "Mechanism-Based Facilitated Maturation of Human Pluripotent Stem Cell-Derived Cardiomyocytes," *Circ Arrhythm Electrophysiol.*, 6:191-201.
Lu et al., (2002) "Stereospecific Actication of Cardiac ATP-Sensitive K+ Channels by Epoxyeicosatrienoic Acids: A Structural Determinant Study," in *American Society for Pharmacology and Experimental Therapeutics, Molecular Pharmacology*, 62:1076-1083.
Monti et al., (May 2008) "Soluble epoxide hydrolase is a susceptibility factor for heart failure in a rat model of human disease," *Nature Genetics*, 40(5):529-537.
Morisseau et al., (2002) "Structural refinement of inhibitors of urea-based soluble epoxide hydrolases," *Biochemical Pharmacology*, 63:1599-1608. [Published-Evidence-5] [EP 06 772 386].
Morisseau et al., (Aug. 1999) "Potent Urea and Carbanate Inhibitors of Soluble Epoxide Hydrolases," *Proc. Natl. Acd. Sci. USA*, 96:8849-8854.
Ogata, (Aug. 2002) "Stimulation of peroxisome-proliferatoractivated receptor α (PPARα) attenuates cardiac fibrosis and endothelin-1 production in pressure-overloaded rat hearts," *Clinical Science*,103(Suppl. 48):2845-2885. [Published-Evidence-3] [EP 06 772 386].
Sirish et al., (Apr. 2, 2013) "Unique mechanistic insights into the beneficial effects of soluble epoxide hydrolase inhibitors in the prevention of cardiac fibrosis," *Proc. Natl. Acad. Sci.*,110(14):5618-5623.
Sirish et al., (2016) "Molecular Mechanisms and New Treatment Paradigm for Atrial Fibrillation," and Data Supplement, *Circ Arrhythm Electrophysiol.*, 9:e003721, 33pp.
Sirna et al., (1990) "Cardiac Evaluation of the Patient With Stroke," *Stroke*, 21:14-23.
Templin et al., "Transplantation and Tracking of Human-Induced Pluripotent Stem Cells in a Pig Model of Myocardial Infarction," *Circulation*, 126, Jul. 23, 2012, pp. 430-439. <doi: 10.1161/CIRCULATIONAHA.111.087684>.
Xu, Danyan et al., (Dec. 5, 2006) "Prevention and reversal of cardiac hypertrophy by soluble epoxide hydrolase inhibitors," *PNAS*, 103(49):18733-18738.
Yoshida et al., (2017) "Induced Pluripotent Stem Cells 10 Years Later for Cardiac Applications," *Circ Res.*, 120:1958-1968. [Abstract Only].
Youssef et al., "The Promise and Challenge of Induced Pluripotent Stem Cells for Cardiovascular Applications," JACC: Basic to Translational Science, vol. 1, No. 6, Oct. 31, 2016, pp. 510-523.
Zhao et al., (2004) "Soluble Epoxide Hydrolase Inhibition Protects the Kidney from Hypertension-Induced Damage" in *Journal of American Society of Nephrology*, 15:1244-1253.

(56) References Cited

OTHER PUBLICATIONS

Ingulli, E. et al. (Jan. 2010). "Mechanism of cellular rejection in transplantation," *Pediatr Nephrol* 25(1):61-74.

* cited by examiner

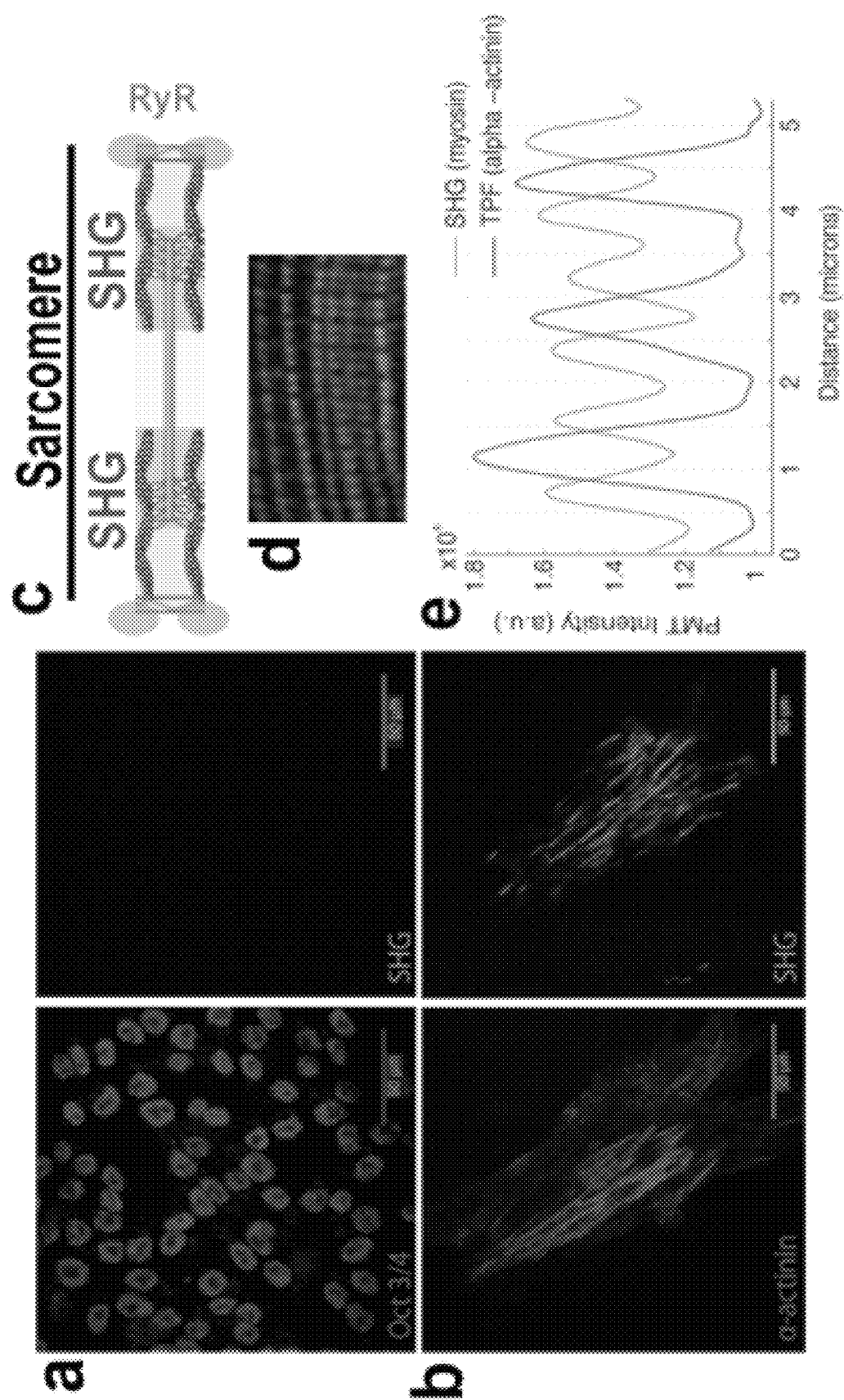
Fig. 11A-E

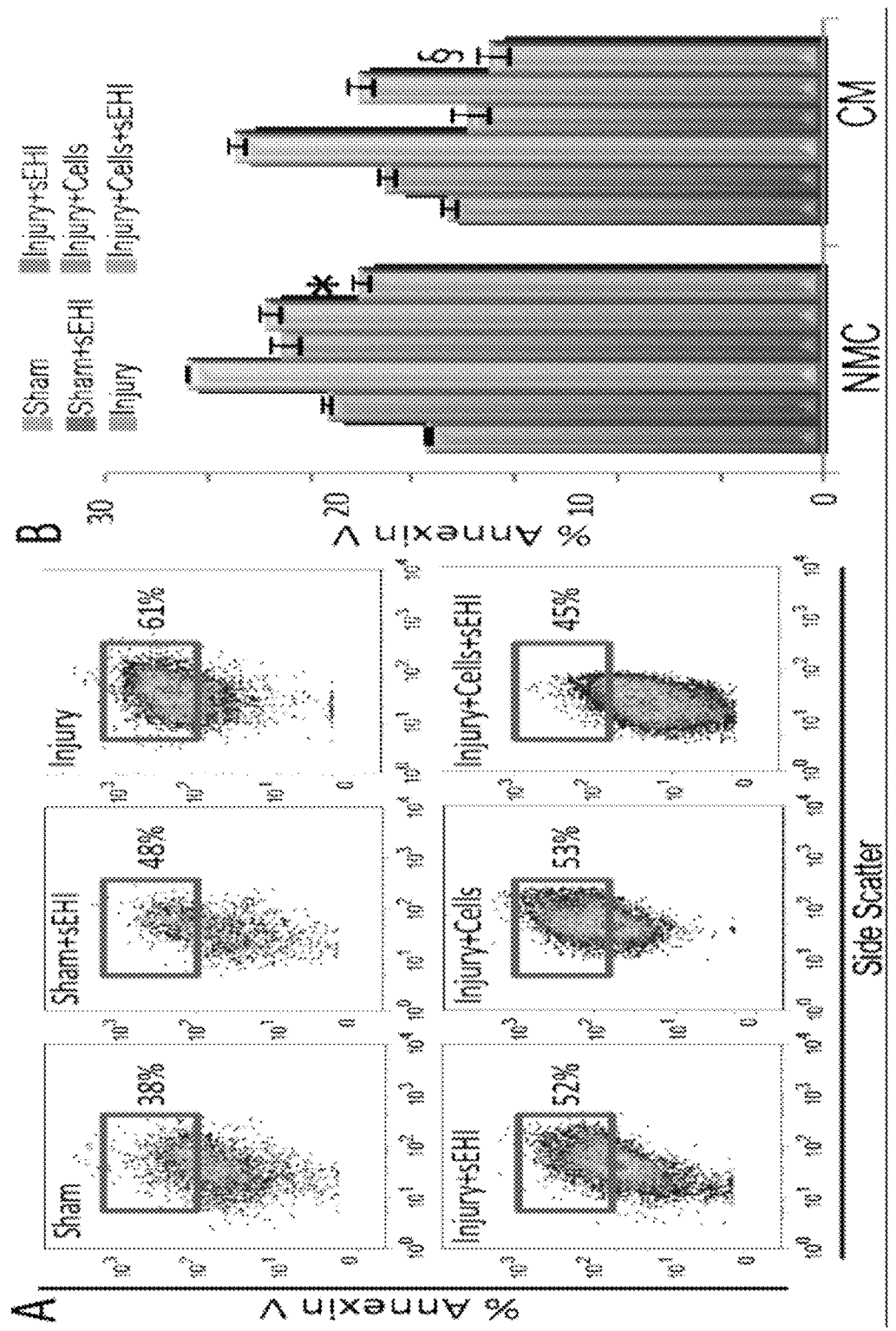
*Fig. 12A-B*

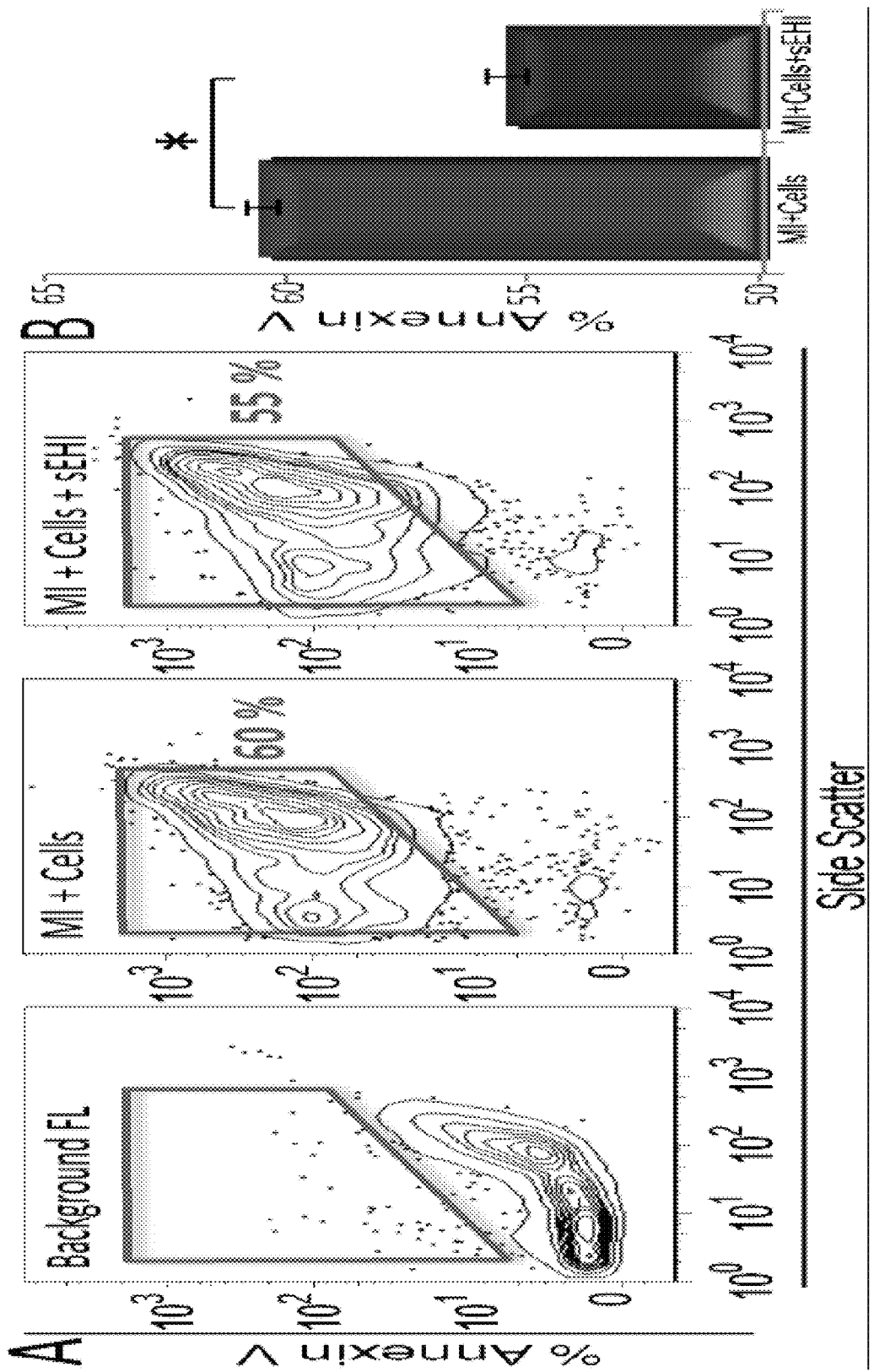
Fig. 13A-B

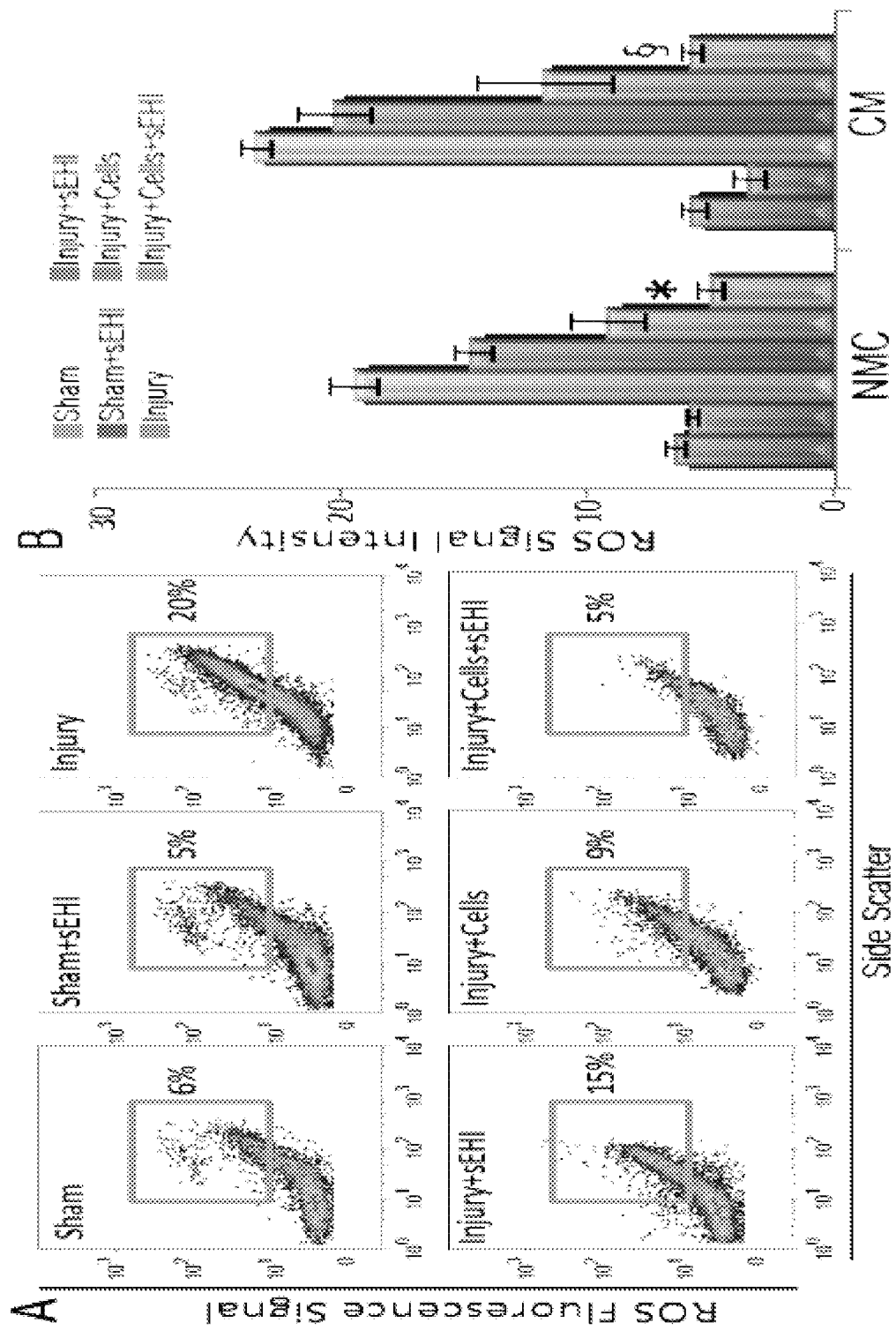
Fig. 14A-B

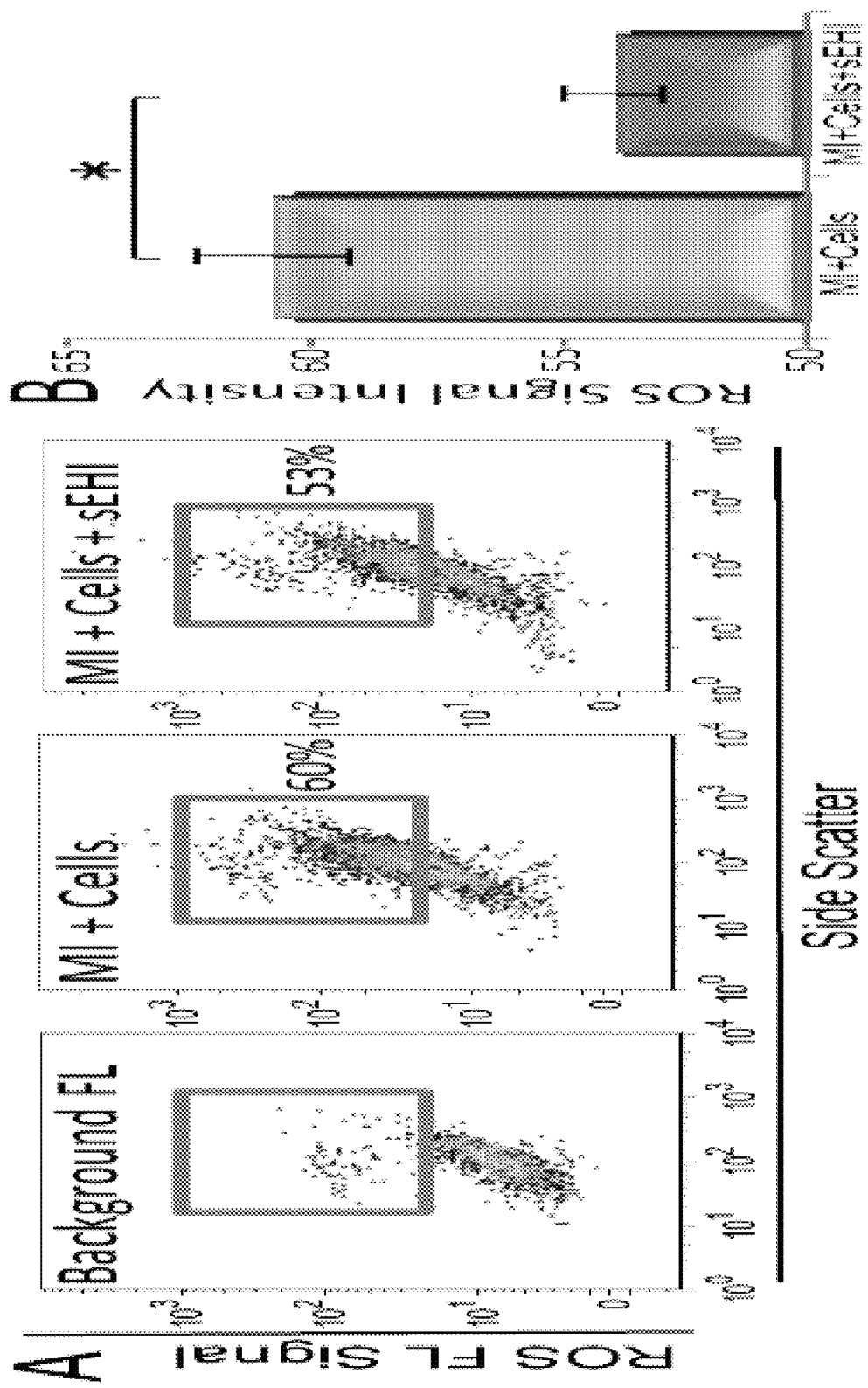
Fig. 15A-B

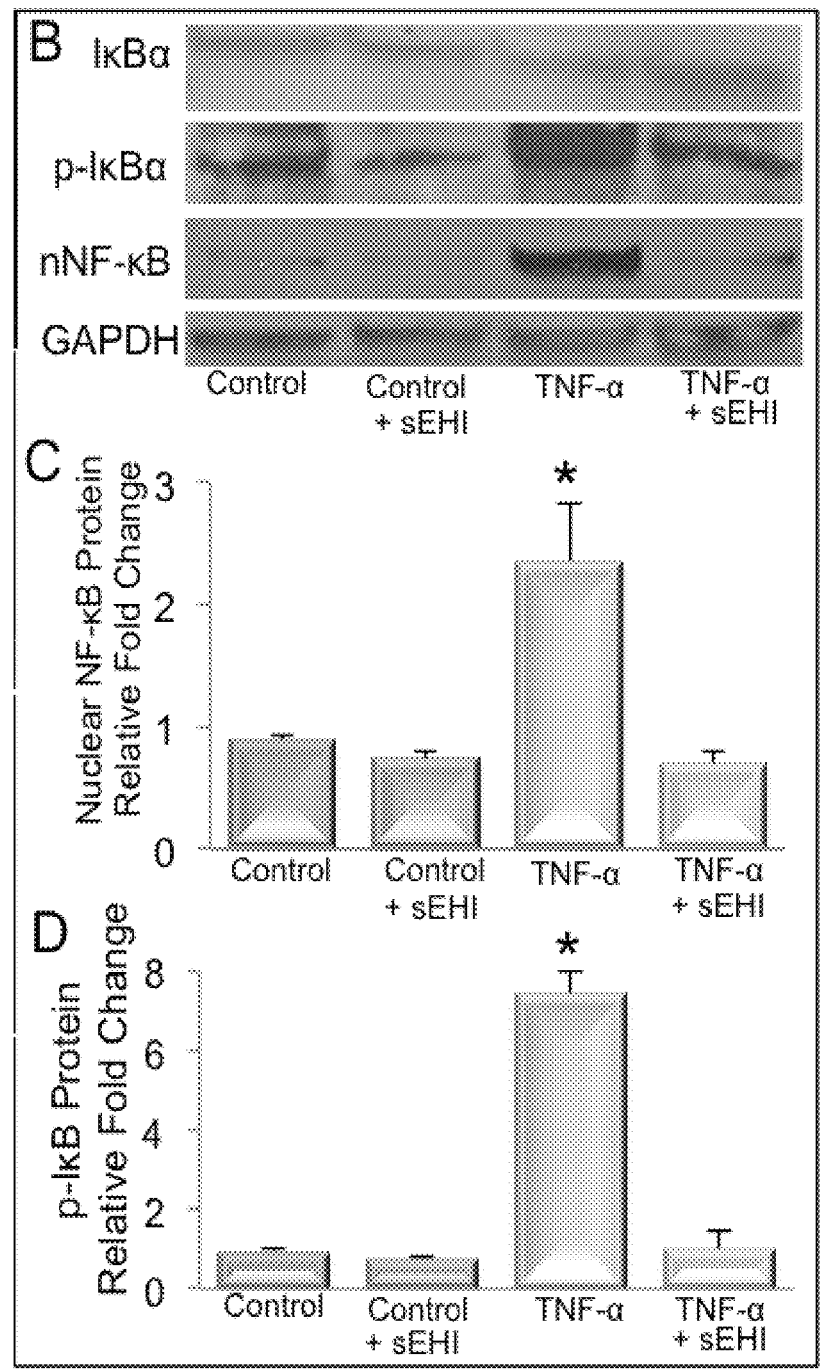
Fig. 16B-D

SEQUENCE LISTING

<160> NUMBER OF SEQ ID NOS: 40

<210> SEQ ID NO 1
<211> LENGTH: 554
<212> TYPE: PRT
<213> ORGANISM: Homo sapiens

<400> SEQUENCE: 1

```
Met Thr Leu Arg Gly Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Gly Pro Glu Gly
        35                  40                  45

Ala Thr Thr Arg Leu Met Lys Gly Glu Ile Thr Leu Ser Gln Trp Ile
    50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
            260                 265                 270

Trp Arg Tyr Gln Ile Pro Ala Leu Ala Gln Ala Gly Tyr Arg Val Leu
        275                 280                 285

Ala Met Asp Met Lys Gly Tyr Gly Glu Ser Ser Ala Pro Pro Glu Ile
    290                 295                 300

Glu Glu Tyr Cys Met Glu Val Leu Cys Lys Glu Met Val Thr Phe Leu
305                 310                 315                 320

Asp Lys Leu Gly Leu Ser Gln Ala Val Phe Ile Gly His Asp Trp Gly
                325                 330                 335

Gly Met Leu Val Trp Tyr Met Ala Leu Phe Tyr Pro Glu Arg Val Arg
            340                 345                 350

Ala Val Ala Ser Leu Asn Thr Pro Phe Ile Pro Ala Asn Pro Asn Met
        355                 360                 365
```

```
Ser Pro Leu Glu Ser Ile Lys Ala Asn Pro Val Phe Asp Tyr Gln Leu
    370                 375                 380

Tyr Phe Gln Glu Pro Gly Val Ala Glu Ala Glu Leu Glu Gln Asn Leu
385                 390                 395                 400

Ser Arg Thr Phe Lys Ser Leu Phe Arg Ala Ser Asp Glu Ser Val Leu
                405                 410                 415

Ser Met His Lys Val Cys Glu Ala Gly Gly Leu Phe Val Asn Ser Pro
                420                 425                 430

Glu Glu Pro Ser Leu Ser Arg Met Val Thr Glu Glu Ile Gln Phe
            435                 440                 445

Tyr Val Gln Gln Phe Lys Lys Ser Gly Phe Arg Gly Pro Leu Asn Trp
450                 455                 460

Tyr Arg Asn Met Glu Arg Asn Trp Lys Trp Ala Cys Lys Ser Leu Gly
465                 470                 475                 480

Arg Lys Ile Leu Ile Pro Ala Leu Met Val Thr Ala Glu Lys Asp Phe
                485                 490                 495

Val Leu Val Pro Gln Met Ser Gln His Met Glu Asp Trp Ile Pro His
                500                 505                 510

Leu Lys Arg Gly His Ile Glu Asp Cys Gly His Trp Thr Gln Met Asp
            515                 520                 525

Lys Pro Thr Glu Val Asn Gln Ile Leu Ile Lys Trp Leu Asp Ser Asp
            530                 535                 540

Ala Arg Asn Pro Pro Val Val Ser Lys Met
545                 550

<210> SEQ ID NO 2
<211> LENGTH: 2100
<212> TYPE: DNA
<213> ORGANISM: Homo sapiens

<400> SEQUENCE: 2
ggcacgagct ctctctctct ctctctctct ctctcgccgc catgacgctg cgcggcgccg     60
tcttcgacct tgacggggtg ctggcgctgc cagcggtgtt cggcgtcctc ggccgcacgg    120
aggaggcccc ggcgctgccc agaggacttc tgaatgatgc tttccagaaa ggggaccag    180 agggtgccac tacccggctt atgaaaggag agatcacact ttcccagtgg ataccactca    240
tggaagaaaa ctgcaggaag tgctccgaga ccgctaaagt ctgcctcccc aagaatttct    300
ccataaaaga aatctttgac aaggcgattt cagccagaaa gatcaaccgc ccatgctcc     360 aggcagctct catgctcagg aagaaaggat tcactactgc catcctcacc aacacctggc    420
tggacgaccg tgctgagaga gatggcctgg cccagctgat gtgtgagctg aagatgcact    480
ttgacttcct gatagagtcg tgtcaggtgg aatggtcaa acctgaacct agatctaca     540 agtttctgct ggacaccctg aaggccagcc ccagtgaggt cgttttttg gatgacatcg    600 gggctaatct gaagccagcc cgtgacttgg aatggtcac catcctggtc caggacactg    660
acacggccct gaaagaactg agaaagtga ccggaatcca gcttctcaat accccggccc    720
ctctgccgac tcttgcaat ccaagtgaca tgagccatgg gtacgtgaca gtaaagccca    780
gggtccgtct gcattttgtg gagctgggct ggcctgctgt gtgcctctgc catggatttc    840
ccgagagttg gtattcttgg aggtaccaga tccctgctct ggcccaggca ggttaccggg    900
tcctagctat ggacatgaaa ggctatggag agtcatctgc tcctcccgaa atagaagaat   960
attgcatgga agtgttatgt aaggagatgg taaccttcct ggataaactg ggcctctctc   1020
aagcagtgtt cattggccat gactggggtg gcatgctggt gtggtacatg gctctcttct   1080
```

```
accccgagag agtgagggcg gtggccagtt tgaatactcc cttcatacca gcaaatccca    1140
acatgtcccc tttggagagt atcaaagcca acccagtatt tgattaccag ctctacttcc    1200
aagaaccagg agtggctgag gctgaactgg aacagaacct gagtcggact ttcaaaagcc    1260
tcttcagagc aagcgatgag agtgttttat ccatgcataa agtctgtgaa gcgggaggac    1320
tttttgtaaa tagcccagaa gagcccagcc tcagcaggat ggtcactgag gaggaaatcc    1380
agttctatgt gcagcagttc aagaagtctg gtttcagagg tcctctaaac tggtaccgaa    1440
acatggaaag gaactggaag tgggcttgca aaagcttggg acggaagatc ctgattccgg    1500
ccctgatggt cacggcggag aaggacttcg tgctcgttcc tcagatgtcc cagcacatgg    1560
aggactggat tccccacctg aaaaggggac acattgagga ctgtgggcac tggacacaga    1620
tggacaagcc aaccgaggtg aatcagatcc tcattaagtg gctggattct gatgcccgga    1680
acccaccggt ggtctcaaag atgtagaacg cagcgtagtg cccacgctca gcaggtgtgc    1740
catccttcca cctgctgggg caccattctt agtatacaga ggtggcctta cacacatctt    1800
gcatggatgg cagcattgtt ctgaaggggt ttgcagaaaa aaagattttt ctttacataa    1860
agtgaatcaa atttgacatt attttagatc ccagagaaat caggtgtgat tagttctcca    1920
ggcatgaatg catcgtccct ttatctgtaa gaacccttag tgtcctgtag ggggacagaa    1980
tggggtggcc agtggtgat ttctctttga ccaatgcata gtttggcaga aaaatcagcc    2040
gttcatttag aagaatctta gcagagattg ggatgcctta ctcaataaag ctaagatgac    2100

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagtgttcat tggccatgac tgg                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
guguucauug gccaugacut t                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
agucauggcc aaugaacact t                                                21
```

```
<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaggctat ggagagtcat ctg                                                  23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
aaggcuaugg agagucauct t                                                    21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gaugacucuc cauagccuut t                                                    21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaggctatg gagagtcatc tgc                                                  23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
aggcuaugga gagucaucut t                                                    21

<210> SEQ ID NO 11
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
agaugacucu ccauagccut t                                              21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caagcagtgt tcattggcca tga                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agcaguguuc auuggccaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
auggccaaug aacacugcut t                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcacatgg aggactggat tcc                                            23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 16
gcacauggag gacuggauut t                                            21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
aauccagucc uccaugugct t                                            21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 ttcaagaga                                                           9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagtgttcat tggccatgac tgg                                          23

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatccccgtg ttcattggcc atgactttca agagaagtca tggccaatga acactttt    59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agctaaaaag tgttcattgg ccatgacttc tcttgaaagt catggccaat gaacacggg   59

<210> SEQ ID NO 22
<211> LENGTH: 23
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 22
gaaaggctat ggagagtcat ctg                                            23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatccccaag gctatggaga gtcatcttca agagagatga ctctccatag ccttttttt    59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agctaaaaaa aggctatgga gagtcatctc tcttgaagat gactctccat agccttggg    59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaggctatg gagagtcatc tgc                                            23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatccccagg ctatggagag tcatctttca agagaagatg actctccata gccttttt     59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agctaaaaaa ggctatggag agtcatcatc tcttgaaaga tgactctcca tagcctggg    59

<210> SEQ ID NO 28
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 28
caagcagtgt tcattggcca tga                                              23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatccccagc agtgttcatt ggccatttca agagaatggc caatgaacac tgcttttt       59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agctaaaaaa gcagtgttca ttggccattc tcttgaaatg gccaatgaac actgctggg      59

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagcacatgg aggactggat tcc                                              23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatccccgca catggaggac tggattttca agagaaatcc agtcctccat gtgctttttt     59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agctaaaaag cacatggagg actggatttc tcttgaaaat ccagtcctcc atgtgcggg      59

<210> SEQ ID NO 34
<211> LENGTH: 20
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 34
uguccagugc ccacaguccu                                                     20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uucccaccug acacgacucu                                                     20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
guucagccuc agccacuccu                                                     20

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aguccucccg cuucacaga                                                      19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gcccacuucc aguccuuuc c                                                    21

<210> SEQ ID NO 39
<211> LENGTH: 2196
<212> TYPE: DNA
<213> ORGANISM: Homo sapiens

<400> SEQUENCE: 39
ctgggcgggt catgcgccct ggccttcgcg catctcccag gttagctgcg tgtccgggtg         60
ctaggctgca gacccgccgc catgacgctg cgcgcggccg tcttcgacct tgacggggtg        120
ctggcgctgc cagcggtgtt cggcgtcctc ggccgcacgg aggaggccct ggcgctgccc        180
agaggacttc tgaatgatgc tttccagaaa gggggaccag agggtgccac tacccggctt        240
atgaaaggag agatcacact ttcccagtgg ataccactca tggaagaaaa ctgcaggaag        300
tgctccgaga ccgctaaagt ctgcctcccc aagaatttct ccataaaaga aatctttgac        360
```

| | |
|---|---|
| aaggcgattt cagccagaaa gatcaaccgc cccatgctcc aggcagctct catgctcagg | 420 |
| aagaaaggat tcactactgc catcctcacc aacacctggc tggacgaccg tgctgagaga | 480 |
| gatggcctgg cccagctgat gtgtgagctg aagatgcact ttgacttcct gatagagtcg | 540 |
| tgtcaggtgg gaatggtcaa acctgaacct cagatctaca agtttctgct ggacaccctg | 600 |
| aaggccagcc ccagtgaggt cgttttttg gatgacatcg gggctaatct gaagccagcc | 660 |
| cgtgacttgg gaatggtcac catcctggtc caggacactg acacggccct gaaagaactg | 720 |
| gagaaagtga ccggaatcca gcttctcaat accccggccc ctctgccgac ctcttgcaat | 780 |
| ccaagtgaca tgagccatgg gtacgtgaca gtaaagccca gggtccgtct gcattttgtg | 840 |
| gagctgggct ccggccctgc tgtgtgcctc tgccatggat ttcccgagag ttggtattct | 900 |
| tggaggtacc agatccctgc tctggcccag gcaggttacc gggtcctagc tatggacatg | 960 |
| aaaggctatg gagagtcatc tgctcctccc gaaatagaag aatattgcat ggaagtgtta | 1020 |
| tgtaaggaga tggtaacctt cctggataaa ctgggcctct ctcaagcagt gttcattggc | 1080 |
| catgactggg gtggcatgct ggtgtggtac atggctctct tctaccccga gagagtgagg | 1140 |
| gcggtggcca gtttgaatac tcccttcata ccagcaaatc caacatgtc cccttttggag | 1200 |
| agtatcaaag ccaacccagt atttgattac cagctctact ccaagaacc aggagtggct | 1260 |
| gaggctgaac tggaacagaa cctgagtcgg actttcaaaa gcctcttcag agcaagcgat | 1320 |
| gagagtgttt atccatgca taaagtctgt gaagcgggag acttttttgt aaatagccca | 1380 |
| gaagagccca gcctcagcag gatggtcact gaggaggaaa tccagttcta tgtgcagcag | 1440 |
| ttcaagaagt ctggtttcag aggtcctcta aactggtacc gaaacatgga aaggaactgg | 1500 |
| aagtgggctt gcaaaagctt gggacggaag atcctgattc cggccctgat ggtcacggcg | 1560 |
| gagaaggact tcgtgctcgt tcctcagatg tcccagcaca tggaggactg gattccccac | 1620 |
| ctgaaaaggg gacacattga ggactgtggg cactggacac agatggacaa gccaaccgag | 1680 |
| gtgaatcaga tcctcattaa gtggctggat tctgatgccc ggaacccacc ggtggtctca | 1740 |
| aagatgtaga acgcagcgtg tgcccacgct cagcaggtgt gccatccttc cacctgctgg | 1800 |
| ggcaccattc ttagtataca gaggtggcct tacacacatc ttgcatggat ggcagcattg | 1860 |
| ttctgaaggg gtttgcagaa aaaaagatt ttctttacat aaagtgaatc aaatttgaca | 1920 |
| ttattttaga tcccagagaa atcaggtgtg attagttctc caggcatgaa tgcatcgtcc | 1980 |
| ctttatctgt aagaaccctt agtgtcctgt aggggggacag aatggggtgg ccaggtggtg | 2040 |
| atttctcttt gaccaatgca tagtttggca gaaaaatcag ccgttcattt agaagaatct | 2100 |
| tagcagagat tgggatgcct tactcaataa agctaagatg actatgctgc tggctgtctt | 2160 |
| tgttcttgga gaggtggagt gactgttcac ggagaa | 2196 |

<210> SEQ ID NO 40
<211> LENGTH: 555
<212> TYPE: PRT
<213> ORGANISM: Homo sapiens

<400> SEQUENCE: 40

Met Thr Leu Arg Ala Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Gly Pro Glu Gly
        35                  40                  45

```
Ala Thr Thr Arg Leu Met Lys Gly Glu Ile Thr Leu Ser Gln Trp Ile
    50                  55                  60

Pro Leu Met Glu Glu Asn Cys Arg Lys Cys Ser Glu Thr Ala Lys Val
 65              70                  75                  80

Cys Leu Pro Lys Asn Phe Ser Ile Lys Glu Ile Phe Asp Lys Ala Ile
                 85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
            115                 120                 125

Asp Arg Ala Glu Arg Asp Gly Leu Ala Gln Leu Met Cys Glu Leu Lys
130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
            195                 200                 205

Ala Leu Lys Glu Leu Glu Lys Val Thr Gly Ile Gln Leu Leu Asn Thr
210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Ser Gly Pro Ala Val Cys Leu Cys His Gly Phe Pro Glu Ser Trp Tyr
            260                 265                 270

Ser Trp Arg Tyr Gln Ile Pro Ala Leu Ala Gln Ala Gly Tyr Arg Val
            275                 280                 285

Leu Ala Met Asp Met Lys Gly Tyr Gly Glu Ser Ser Ala Pro Pro Glu
290                 295                 300

Ile Glu Glu Tyr Cys Met Glu Val Leu Cys Lys Glu Met Val Thr Phe
305                 310                 315                 320

Leu Asp Lys Leu Gly Leu Ser Gln Ala Val Phe Ile Gly His Asp Trp
                325                 330                 335

Gly Gly Met Leu Val Trp Tyr Met Ala Leu Phe Tyr Pro Glu Arg Val
            340                 345                 350

Arg Ala Val Ala Ser Leu Asn Thr Pro Phe Ile Pro Ala Asn Pro Asn
            355                 360                 365

Met Ser Pro Leu Glu Ser Ile Lys Ala Asn Pro Val Phe Asp Tyr Gln
370                 375                 380

Leu Tyr Phe Gln Glu Pro Gly Val Ala Glu Ala Glu Leu Glu Gln Asn
385                 390                 395                 400

Leu Ser Arg Thr Phe Lys Ser Leu Phe Arg Ala Ser Asp Glu Ser Val
                405                 410                 415

Leu Ser Met His Lys Val Cys Glu Ala Gly Gly Leu Phe Val Asn Ser
            420                 425                 430

Pro Glu Glu Pro Ser Leu Ser Arg Met Val Thr Glu Glu Ile Gln
            435                 440                 445

Phe Tyr Val Gln Gln Phe Lys Lys Ser Gly Phe Arg Gly Pro Leu Asn
450                 455                 460

Trp Tyr Arg Asn Met Glu Arg Asn Trp Lys Trp Ala Cys Lys Ser Leu
```

-continued

```
465                 470                 475                 480

Gly Arg Lys Ile Leu Ile Pro Ala Leu Met Val Thr Ala Glu Lys Asp
                485                 490                 495

Phe Val Leu Val Pro Gln Met Ser Gln His Met Glu Asp Trp Ile Pro
                500                 505                 510

His Leu Lys Arg Gly His Ile Glu Asp Cys Gly His Trp Thr Gln Met
                515                 520                 525

Asp Lys Pro Thr Glu Val Asn Gln Ile Leu Ile Lys Trp Leu Asp Ser
                530                 535                 540

Asp Ala Arg Asn Pro Pro Val Val Ser Lys Met
545                 550                 555
```

METHODS OF IMPROVING CELL-BASED THERAPY

CROSS-REFERENCE TO RELATED APPLICATIONS

This application is a continuation of U.S. application Ser. No. 14/737,263, filed on Jun. 11, 2015, which claims the benefit under 35 U.S.C. § 119(e) of U.S. Provisional Application No. 62/012,422, filed on Jun. 16, 2014, which are hereby incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Sep. 9, 2015, is named UCDVP108_SL.txt and is 24,959 bytes in size.

FIELD

Provided are methods for improving the efficacy and success of cell-based therapies by co-administration of stem cells with an agent that increases the production and/or level of epoxygenated fatty acids, as well as kits, stents and patches for co-administering stem cells with an agent that increases the production and or levels of EETs.

BACKGROUND

Cardiovascular disease (CVD) is the leading cause of death for both men and women in the United States. Since cardiac myocytes have limited ability to regenerate, their malfunction or significant loss due to aging or diseases can lead to lethal consequences. Recent studies have provided exciting evidence to support the notion that stem cells may offer an enormous potential for regenerative therapy. However one intractable barrier to cell therapy in all tissues is overcoming the confounding hurdle of scars that ensue from acute and robust inflammatory responses arising during tissue injury.

CVD is the leading cause of morbidity and mortality in the US (9-12). Therapeutic strategies using cell-based therapy to combat ischemic cardiomyopathy have not produced full restorative functions (13-15). Moreover, previous studies have demonstrated that transplanted stem cells do not engraft or survive long term due to apoptosis, increased collagen deposition, ischemic environment, and increased inflammation related factors such as free radicals and cytokines in the host myocardium (16-18).

Arachidonic acid is released in response to tissue injury and can be metabolized through the cyclooxygenase (COX), lipoxygenase (LOX) and cytochrome P450 (CYP450) pathways (FIG. 1). The CYP450 epoxygenase pathway generates epoxyeicosatrienoic acids (EETs) which modulate ion transport and gene expression, producing vasorelaxation, anti-inflammatory and pro-fibrinolytic effects (19). EETs are further metabolized by soluble epoxide hydrolases (sEH) to form the corresponding dihydroxyeicosatrienoic acids (DHETs) with a significant reduction in anti-hypertensive and anti-inflammatory activities (19-21).

SUMMARY

In one aspect, provided are methods of increasing, improving and/or promoting the survival, engraftment, and/or integration of transplanted stem cells in a tissue of a subject in need thereof, comprising co-administering to the subject the stem cells with an agent that increases the production and/or level of epoxygenated fatty acids.

In varying embodiments, the cardiomyopathy is hypertrophic cardiomyopathy. In varying embodiments, the cardiomyopathy is hypertensive cardiomyopathy. In varying embodiments, the cardiomyopathy is diabetic cardiomyopathy. In varying embodiments, the cardiomyopathy is due to valvular heart disease. In varying embodiments, the valvular heart disease is secondary to rheumatic fever, myxomatous degeneration of the valve, or papillary muscle dysfunction. In varying embodiments, the cardiomyopathy is due to myocardial infarction. In varying embodiments, the cardiomyopathy is due to familial hypertrophic cardiomyopathy. In varying embodiments, the cardiomyopathy is dilated cardiomyopathy. In varying embodiments, the dilated cardiomyopathy is alcohol-induced cardiomyopathy. In varying embodiments, the dilated cardiomyopathy is viral-induced cardiomyopathy. In varying embodiments, the dilated cardiomyopathy is familial dilated cardiomyopathy. In varying embodiments, the dilated cardiomyopathy is idiopathic cardiomyopathy. In varying embodiments, the dilated cardiomyopathy is caused by administration of an anti-cancer drug or exposure to a toxic agent. In varying embodiments, the administration of said stem cells and said agent or agents inhibits cardiac arrhythmia. In some embodiments, the arrhythmia is atrial fibrillation or atrial flutter. In some embodiments, the arrhythmia is ventricular fibrillation. In some embodiments, the arrhythmia is ventricular tachycardia.

In varying embodiments of the methods, the agent comprises one or more epoxygenated fatty acids. In varying embodiments, the epoxygenated fatty acids are selected from the group consisting of cis-epoxyeicosatrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In varying embodiments, the agent increases the production and/or levels of cis-epoxyeicosatrienoic acids ("EETs"). In varying embodiments of the methods, the agent that increases the production and/or level of EETs is an inhibitor of soluble epoxide hydrolase ("sEH"). In varying embodiments, the inhibitor of sEH comprises a primary pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM. In varying embodiments of the methods, the inhibitor of sEH is selected from the group consisting of:

a) 3-(4-chlorophenyl)-1-(3,4-dichlorphenyl)urea or 3,4, 4'-trichlorocarbanilide (TCC; compound 295);

b) 12-(3-adamantan-1-yl-ureido) dodecanoic acid (AUDA; compound 700);

c) 1-adamantanyl-3-{5-[2-(2-ethoxyethoxy)ethoxy]pentyl]}urea (AEPU; compound 950);

d) 1-(1-acetypiperidin-4-yl)-3-adamantanylurea (APAU; compound 1153);

e) trans-4-[4-(3-Adamantan-1-yl-ureido)-cyclohexyloxy]-benzoic acid (tAUCB; compound 1471);

f) cis-4-[4-(3-Adamantan-1-yl-ureido)-cyclohexyloxy]-benzoic acid (cAUCB; compound 1686);

g) 1-(1-methylsulfonyl-piperidin-4-yl)-3-(4-trifluoromethoxy-phenyl)-urea (TUPS; compound 1709);

h) trans-4-{4-[3-(4-Trifluoromethoxy-phenyl)-ureido]-cyclohexyloxy}-benzoic acid (tTUCB; compound 1728);

i) 1-trifluoromethoxyphenyl-3-(1-propionylpiperidin-4-yl) urea (TPPU; compound 1770);

j) 1-(1-ethyl sulfonyl-piperidin-4-yl)-3-(4-trifluoromethoxy-phenyl)-urea (TUPSE; compound 2213);

k) 1-(1-(cyclopropanecarbonyl)piperidin-4-yl)-3-(4-(trifluoromethoxy)phenyl)urea (CPTU; compound 2214);

l) trans-N-methyl-4-[4-(3-Adamantan-1-yl-ureido)-cyclohexyloxy]-benzamide (tMAUCB; compound 2225);

m) trans-N-methyl-4-[4-((3-trifluoromethyl-4-chlorophenyl)-ureido)-cyclohexyloxy]-benzamide (tMTCUCB; compound 2226);

n) cis-N-methyl-4-{4-[3-(4-trifluoromethoxy-phenyl)-ureido]-cyclohexyloxy}-benzamide (cMTUCB; compound 2228); and o) 1-cycloheptyl-3-(3-(1,5-diphenyl-1H-pyrazol-3-yl)propyl)urea (HDP3U; compound 2247).

In varying embodiments of the methods, the inhibitor of sEH is selected from the group consisting of:

a) 3-(4-chlorophenyl)-1-(3,4-dichlorphenyl)urea or 3,4,4'-trichlorocarbanilide (TCC; compound 295);

b) 12-(3-adamantan-1-yl-ureido) dodecanoic acid (AUDA; compound 700);

c) 1-adamantanyl-3-{5-[2-(2-ethoxyethoxy)ethoxy]pentyl]}urea (AEPU; compound 950);

d) 1-(1-acetypiperidin-4-yl)-3-adamantanylurea (APAU; compound 1153);

e) trans-4-[4-(3-Adamantan-1-yl-ureido)-cyclohexyloxy]-benzoic acid (tAUCB; compound 1471);

f) cis-4-[4-(3-Adamantan-1-yl-ureido)-cyclohexyloxy]-benzoic acid (cAUCB; compound 1686);

g) trans-4-{4-[3-(4-Trifluoromethoxy-phenyl)-ureido]-cyclohexyloxy}-benzoic acid (tTUCB; compound 1728);

h) trans-N-methyl-4-[4-(3-Adamantan-1-yl-ureido)-cyclohexyloxy]-benzamide (tMAUCB; compound 2225);

i) trans-N-methyl-4-[4-((3-trifluoromethyl-4-chlorophenyl)-ureido)-cyclohexyloxy]-benzamide (tMTCUCB; compound 2226);

j) cis-N-methyl-4-{4-[3-(4-trifluoromethoxy-phenyl)-ureido]-cyclohexyloxy}-benzamide (cMTUCB; compound 2228); and k) 1-cycloheptyl-3-(3-(1,5-diphenyl-1H-pyrazol-3-yl)propyl)urea (HDP3U; compound 2247).

In varying embodiments of the methods, the inhibitor of sEH is selected from the group consisting of:

a) trans-4-[4-(3-Adamantan-1-yl-ureido)-cyclohexyloxy]-benzoic acid (tAUCB; compound 1471);

b) 4-{4-[3-(4-Trifluoromethoxy-phenyl)-ureido]-cyclohexyloxy}-benzoic acid (tTUCB; compound 1728);

c) 1-trifluoromethoxyphenyl-3-(1-propionylpiperidin-4-yl) urea (TPPU; compound 1770);

d) trans-2-(4-(4-(3-(4-trifluoromethoxy-phenyl)-ureido)-cyclohexyloxy)-benzamido)-acetic acid (compound 2283);

e) N-(methylsulfonyl)-4-(trans-4-(3-(4-trifluoromethoxyphenyl)-ureido)-cyclohexyloxy)-benzamide (compound 2728);

f) 1-(trans-4-(4-(1H-tetrazol-5-yl)-phenoxy)-cyclohexyl)-3-(4-(trifluoromethoxy)-phenyl)-urea (compound 2806);

g) 4-(trans-4-(3-(2-fluorophenyl)-ureido)-cyclohexyloxy)-benzoic acid (compound 2736);

h) 4-(4-(3-(4-(trifluoromethoxy)-phenyl)-ureido)-phenoxy)-benzoic acid (compound 2803);

i) 4-(3-fluoro-4-(3-(4-(trifluoromethoxy)-phenyl)-ureido)-phenoxy)-benzoic acid (compound 2807);

j) N-hydroxy-4-(trans-4-(3-(4-(trifluoromethoxy)-phenyl)-ureido)-cyclohexyloxy)-benzamide (compound 2761);

k) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);

l) 1-(4-oxocyclohexyl)-3-(4-(trifluoromethoxy)-phenyl)-urea (compound 2809);

m) methyl 4-(4-(3-(4-(trifluoromethoxy)-phenyl)-ureido)-cyclohexylamino)-benzoate (compound 2804);

n) 1-(4-(pyrimidin-2-yloxy)-cyclohexyl)-3-(4-(trifluoromethoxy)-phenyl)-urea (compound 2810); and o) 4-(trans-4-(3-(4-(difluoromethoxy)-phenyl)-ureido)-cyclohexyloxy)-benzoic acid (compound 2805).

In varying embodiments of the methods, the inhibitor of sEH is selected from the group consisting of:

a) trans-4-[4-(3-Adamantan-1-yl-ureido)-cyclohexyloxy]-benzoic acid (tAUCB; compound 1471); and b) 1-trifluoromethoxyphenyl-3-(1-propionylpiperidin-4-yl) urea (TPPU; compound 1770).

In varying embodiments of the methods, the inhibitor of sEH is selected from the group consisting of:

a) trans-4-{4-[3-(4-Trifluoromethoxy-phenyl)-ureido]-cyclohexyloxy}-benzoic acid (tTUCB; compound 1728);

b) 1-trifluoromethoxyphenyl-3-(1-propionylpiperidin-4-yl) urea (TPPU; compound 1770); and c) 1-(1-methylsulfonyl-piperidin-4-yl)-3-(4-trifluoromethoxy-phenyl)-urea (TUPS; compound 1709).

In varying embodiments of the methods, the inhibitor of sEH is co-administered at a subtherapeutic dose. In varying embodiments, the subject is a human. In varying embodiments, the stem cells are selected from multipotent stem cells, pluripotent stem cells, and induced pluripotent stem cells. In varying embodiments, the stem cells comprise mesenchymal stem cells. In varying embodiments, the stem cells comprise myocyte stem cells. In some embodiments, the stem cells comprise cardiomyocyte stem cells. In some embodiments, the stem cells comprise adult cardiac stem cells or cardiac progenitor cells derived from human cardiac tissues. In some embodiments, the stem cells are selected from the group consisting of cardiomyocytes or cardiac progenitor cells derived from multipotent stem cells, cardiomyocytes or cardiac progenitor cells derived from pluripotent stem cells, cardiomyocytes or cardiac progenitor cells derived from induced pluripotent stem cells, adult cardiac progenitor cells and cardiac stem cells. In some embodiments, the stem cells are syngeneic to the subject. In some embodiments, the stem cells are allogeneic to the subject. In some embodiments, the stem cells are xenogeneic to the subject. In some embodiments, at least about 1 million ($1 \times 10^6$) to about 1 billion ($1 \times 10^9$) stem cells are administered. In some embodiments, the stem cells are administered intravenously, intra-arterially or intralesionally. In some embodiments, the stem cells and the agent that increases the production and/or level of epoxygenated fatty acids are administered by the same route of administration. In some embodiments, the stem cells and the agent that increases the production and/or level of epoxygenated fatty acids are administered by different routes of administration. In some embodiments, the stem cells and the inhibitor of sEH are concurrently co-administered. In some embodiments, the stem cells and the inhibitor of sEH are sequentially co-administered. In some embodiments, the tissue is cardiac tissue.

In another aspect, provided are kits, stents and patches. In some embodiments, the kits, stents and patches comprise a population of stem cells and one or more agents that increase the production and/or level of epoxygenated fatty acids. In varying embodiments, of the stents, the stent is a coronary artery stent. In varying embodiments of the patches, the patch is a cardiac patch.

In varying embodiments of the kits, stents and patches, the agent comprises one or more epoxygenated fatty acids. In varying embodiments, the epoxygenated fatty acids are selected from the group consisting of cis-epoxyeicosatrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In varying embodiments, the agent increases the production and/or levels of cis-epoxyeicosatrienoic acids ("EETs"). In varying embodiments of the kits, stents and patches, the agent that increases the production and/or level of EETs is an inhibitor of soluble epoxide hydrolase ("sEH"). In varying embodiments, the inhibitor of sEH comprises a primary pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM. In varying embodiments of the kits, stents and patches, the inhibitor of sEH is selected from the group consisting of:

a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl]}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) 1-(1-methylsulfonyl-piperidin-4-yl)-3-(4-trifluoromethoxy-phenyl)-urea (TUPS; compound 1709);
h) trans-4-{4-[3-(4-Trifluoromethoxy-phenyl)-ureido]-cyclohexyloxy}-benzoic acid (tTUCB; compound 1728);
i) 1-trifluoromethoxyphenyl-3-(1-propionylpiperidin-4-yl) urea (TPPU; compound 1770);
j) 1-(1-ethyl sulfonyl-piperidin-4-yl)-3-(4-trifluoromethoxy-phenyl)-urea (TUPSE; compound 2213)
k) 1-(1-(cyclopropanecarbonyl)piperidin-4-yl)-3-(4-(trifluoromethoxy)phenyl)urea (CPTU; compound 2214);
l) trans-N-methyl-4-[4-(3-Adamantan-1-yl-ureido)-cyclohexyloxy]-benzamide (tMAUCB; compound 2225);
m) trans-N-methyl-4-[4-((3-trifluoromethyl-4-chlorophenyl)-ureido)-cyclohexyloxy]-benzamide (tMTCUCB; compound 2226);
n) cis-N-methyl-4-{4-[3-(4-trifluoromethoxy-phenyl)-ureido]-cyclohexyloxy}-benzamide (cMTUCB; compound 2228); and
o) 1-cycloheptyl-3-(3-(1,5-diphenyl-1H-pyrazol-3-yl)propyl)urea (HDP3U; compound 2247).

In varying embodiments of the kits, stents and patches, the inhibitor of sEH is selected from the group consisting of:
a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl]}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) trans-4-{4-[3-(4-Trifluoromethoxy-phenyl)-ureido]-cyclohexyloxy}-benzoic acid (tTUCB; compound 1728);
h) trans-N-methyl-4-[4-(3-Adamantan-1-yl-ureido)-cyclohexyloxy]-benzamide (tMAUCB; compound 2225);
i) trans-N-methyl-4-[4-((3-trifluoromethyl-4-chlorophenyl)-ureido)-cyclohexyloxy]-benzamide (tMTCUCB; compound 2226);
j) cis-N-methyl-4-{4-[3-(4-trifluoromethoxy-phenyl)-ureido]-cyclohexyloxy}-benzamide (cMTUCB; compound 2228); and
k) 1-cycloheptyl-3-(3-(1,5-diphenyl-1H-pyrazol-3-yl)propyl)urea (HDP3U; compound 2247).

In varying embodiments of the kits, stents and patches, the inhibitor of sEH is selected from the group consisting of:
a) trans-4-[4-(3-Adamantan-1-yl-ureido)-cyclohexyloxy]-benzoic acid (tAUCB; compound 1471);
b) 4-{4-[3-(4-Trifluoromethoxy-phenyl)-ureido]-cyclohexyloxy}-benzoic acid (tTUCB; compound 1728);
c) 1-trifluoromethoxyphenyl-3-(1-propionylpiperidin-4-yl) urea (TPPU; compound 1770);
d) trans-2-(4-(4-(3-(4-trifluoromethoxy-phenyl)-ureido)-cyclohexyloxy)-benzamido)-acetic acid (compound 2283);
e) N-(methyl sulfonyl)-4-(trans-4-(3-(4-trifluoromethoxy-phenyl)-ureido)-cyclohexyloxy)-benzamide (compound 2728);
f) 1-(trans-4-(4-(1H-tetrazol-5-yl)-phenoxy)-cyclohexyl)-3-(4-(trifluoromethoxy)-phenyl)-urea (compound 2806);
g) 4-(trans-4-(3-(2-fluorophenyl)-ureido)-cyclohexyloxy)-benzoic acid (compound 2736);
h) 4-(4-(3-(4-(trifluoromethoxy)-phenyl)-ureido)-phenoxy)-benzoic acid (compound 2803);
i) 4-(3-fluoro-4-(3-(4-(trifluoromethoxy)-phenyl)-ureido)-phenoxy)-benzoic acid (compound 2807);
j) N-hydroxy-4-(trans-4-(3-(4-(trifluoromethoxy)-phenyl)-ureido)-cyclohexyloxy)-benzamide (compound 2761);
k) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
l) 1-(4-oxocyclohexyl)-3-(4-(trifluoromethoxy)-phenyl)-urea (compound 2809);
m) methyl 4-(4-(3-(4-(trifluoromethoxy)-phenyl)-ureido)-cyclohexylamino)-benzoate (compound 2804);
n) 1-(4-(pyrimidin-2-yloxy)-cyclohexyl)-3-(4-(trifluoromethoxy)-phenyl)-urea (compound 2810); and
o) 4-(trans-4-(3-(4-(difluoromethoxy)-phenyl)-ureido)-cyclohexyloxy)-benzoic acid (compound 2805).

In varying embodiments of the kits, stents and patches, the inhibitor of sEH is selected from the group consisting of:
a) trans-4-{4-[3-(4-Trifluoromethoxy-phenyl)-ureido]-cyclohexyloxy}-benzoic acid (tTUCB; compound 1728);

b) 1-trifluoromethoxyphenyl-3-(1-propionylpiperidin-4-yl) urea (TPPU; compound 1770); and c) 1-(1-methylsulfonyl-piperidin-4-yl)-3-(4-trifluoromethoxy-phenyl)-urea (TUPS; compound 1709).

In varying embodiments of the kits, stents and patches, the inhibitor of sEH is selected from the group consisting of:

a) trans-4-[4-(3-Adamantan-1-yl-ureido)-cyclohexyloxy]-benzoic acid (tAUCB; compound 1471); and b) 1-trifluoromethoxyphenyl-3-(1-propionylpiperidin-4-yl) urea (TPPU; compound 1770).

In varying embodiments of the kits, stents and patches, the stem cells are selected from multipotent stem cells, pluripotent stem cells, and induced pluripotent stem cells. In varying embodiments, the stem cells comprise mesenchymal stem cells. In varying embodiments, the stem cells comprise myocyte stem cells. In varying embodiments, the stem cells comprise cardiomyocyte stem cells. In varying embodiments, the stem cells are selected from the group consisting of cardiomyocytes or cardiac progenitor cells derived from multipotent stem cells, cardiomyocytes or cardiac progenitor cells derived from pluripotent stem cells, cardiomyocytes or cardiac progenitor cells derived from induced pluripotent stem cells, adult cardiac progenitor cells and cardiac stem cells. In varying embodiments, the population of stem cells comprises at least about 1 million ($1 \times 10^6$) to about 1 billion ($1 \times 10^9$) stem cells.

DEFINITIONS

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH") is an epoxide hydrolase which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

"Valvular heart disease" refers to a disorder of any one of the four valves of the heart. More particularly in the context of the present invention, it refers to conditions in which the disorder increases pressure in a chamber or chambers of the heart. For example, mitral valve insufficiency permits some blood to flow back from the left ventricle into the left atrium rather than into the aorta, increasing the pressure in the atrium.

"Fibrillation," as defined on the website of the American College of Cardiology, is an abnormal, uncontrolled rapid contraction of the fibers in the heart. It further states: "When the process involves the two upper chambers of the heart (the atria), the condition is called 'atrial fibrillation.' When it involves the lower, ventricular chambers, the condition is called 'ventricular fibrillation.'"

An "arrhythmia" is a disorder of the regular rhythmic beating of the heart. As used herein, the term refers to atrial or ventricular fibrillation.

"Arrhythmogenic right ventricular cardiomyopathy" or "ARVC" is a recently recognized form of cardiomyopathy in which electrical disturbances affect the functioning of the right ventricle more than the left ventricle. According to the website of the Cardiomyopathy Association, it is defined as a heart muscle disease characterized by the replacement of heart muscle by fibrous scar and fatty tissue, and has acquired several names, all of which denote the same condition. In addition to ARVC, the most common term, it has also been called Arrhythmogenic Right Ventricular Dysplasia/Cardiomyopathy (ARVD/C) and Arrhythmogenic Right Ventricular Dysplasia (ARVD). It is thought to affect between 1:3,000 and 1:10,000 people.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm C. elegans in the early 1990s and are now known in many species, including humans. As used herein, it refers to exogenously administered miRNA unless specifically noted or otherwise required by context.

With respect to cardiac arrhythmias, "inhibiting" means that the recurrence of such arrhythmias are reduced or eliminated, or that the duration of such arrhythmias is reduced, or both. With respect to cardiac hypertrophy or dilated cardiomyopathy, "inhibiting" means (i) the prevention of the development of the condition in a subject at risk thereof or (ii) in the case of a subject with cardiac hypertrophy, the reversal of hypertrophy.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

The term "therapeutically effective amount" refers to that amount of the compound being administered sufficient to prevent or decrease the development of one or more of the symptoms of the disease, condition or disorder being treated (e.g., fibrosis and/or inflammation).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 65th Ed., 2011, Thomson Healthcare or Brunton, et al., Goodman & Gilman's The Pharmacological Basis of Therapeutics, 12th edition, 2010, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., $21^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., stem cells, an agent that increases epoxygenated fatty acids (e.g., an inhibitor of sEH, an EET, an epoxygenated fatty acid, and mixtures thereof), optionally with an anti-inflammatory agent and/or an analgesic agent) to a mammal so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The term "mesenchymal stem cells" refers to stem cells defined by their capacity to differentiate into bone, cartilage, and adipose tissue. With respect to cell surface markers, MSCs generally express CD44, CD90 and CD105, and do not express CD4, CD34, CD45, CD80, CD86 or MHC-II.

The terms "patient," "subject" or "individual" interchangeably refers to a mammal including a human, a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the fibrosis and/or inflammation in a human or non-human mammalian subject by a measurable amount using any method known in the art. For example, inflammation is inhibited, reduced or decreased if an indicator of inflammation, e.g., swelling, blood levels of prostaglandin PGE2, is at least about 10%, 20%, 30%, 50%, 80%, or 100% reduced, e.g., in comparison to the same inflammatory indicator prior to administration of an agent that increases epoxygenated fatty acids (e.g., an inhibitor of sEH, an EET, an epoxygenated fatty acid, and mixtures thereof). In some embodiments, the fibrosis and/or inflammation is inhibited, reduced or decreased by at least about 1-fold, 2-fold, 3-fold, 4-fold, or more in comparison to the fibrosis and/or inflammation prior to administration of the agent that increases epoxygenated fatty acids (e.g., an inhibitor of sEH, an EET, an epoxygenated fatty acid, and mixtures thereof). Indicators of fibrosis and/or inflammation can also be qualitative.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases epoxygenated fatty acids (e.g., an inhibitor of sEH, an EET, an epoxygenated fatty acid, and mixtures thereof) and/or an anti-inflammatory agent.

BRIEF DESCRIPTION OF THE DRAWINGS

FIGS. 11A-E illustrate second harmonic generation (SHG) signal from hiPSC-CM. a. shows the absence of SHG signal (top right) in hiPSC (red cells labeled with Oct3/4). b, Two photon fluorescence from α-actinin stain (red, left) and the SHG from myosin bundles (green, right) from hiPSC-CM. c, A schematic representation of the SHG signal. d, A row of sarcomeres from cardiomyocytes: SHG signal from the myosin rods (green) and RyR2 (red). e, graphs of the two photon fluorescence and SHG signals.

FIGS. 12A-B illustrate flow cytometric analysis of Annexin V in non-myocyte (NMC) and CM from Sham±sEHI, injury±sEHI and Injury+Cells±sEHI mice (Cells=hiPSC-CM) (B) Summary data from A. * p<0.05. Error bars=SE.

FIGS. 13A-B illustrate flow cytometric analysis of Annexin V in transplanted GFP+ hiPSC-CMs from MI+Cells, and MI+Cells+sEHI mice (Cells=hiPSC-CM) (B) Summary data from A. * p<0.05, Error bars=SE.

FIGS. 14A-B illustrate flow cytometric analysis of Annexin V in non-myocyte (NMC) & CM Sham±sEHI, injury±sEHI & Injury+Cells±sEHI mice (Cells=hiPSC-CM) (B) Summary data from A. * p<0.05. Error bars=SE.

FIGS. 15A-B illustrate flow cytometric analysis of ROS activity in transplanted GFP+ hiPSC-CMs from MI+Cells, and MI+Cells+sEHI mice (Cells=hiPSC-CM) (B) Summary data * p<0.05, Error bars=standard error, FL=fluorescence.

FIGS. 16A-D. A) Prevention of translocation of NF-κB after treatment with sEHI in cultured hiPSC-CMs stimulated with TNF-α. B). Western blot analysis of total IκB, phosphorylated IκB, nuclear NF-κB (nNF-κB) and GAPDH levels. C) & D) Quantification of Nuclear NF-κB and pIκB respectively normalized to GAPDH. Scale bar=200 μM. *p<0.05 n=3/group.

DETAILED DESCRIPTION

1. Introduction

Figure 1:
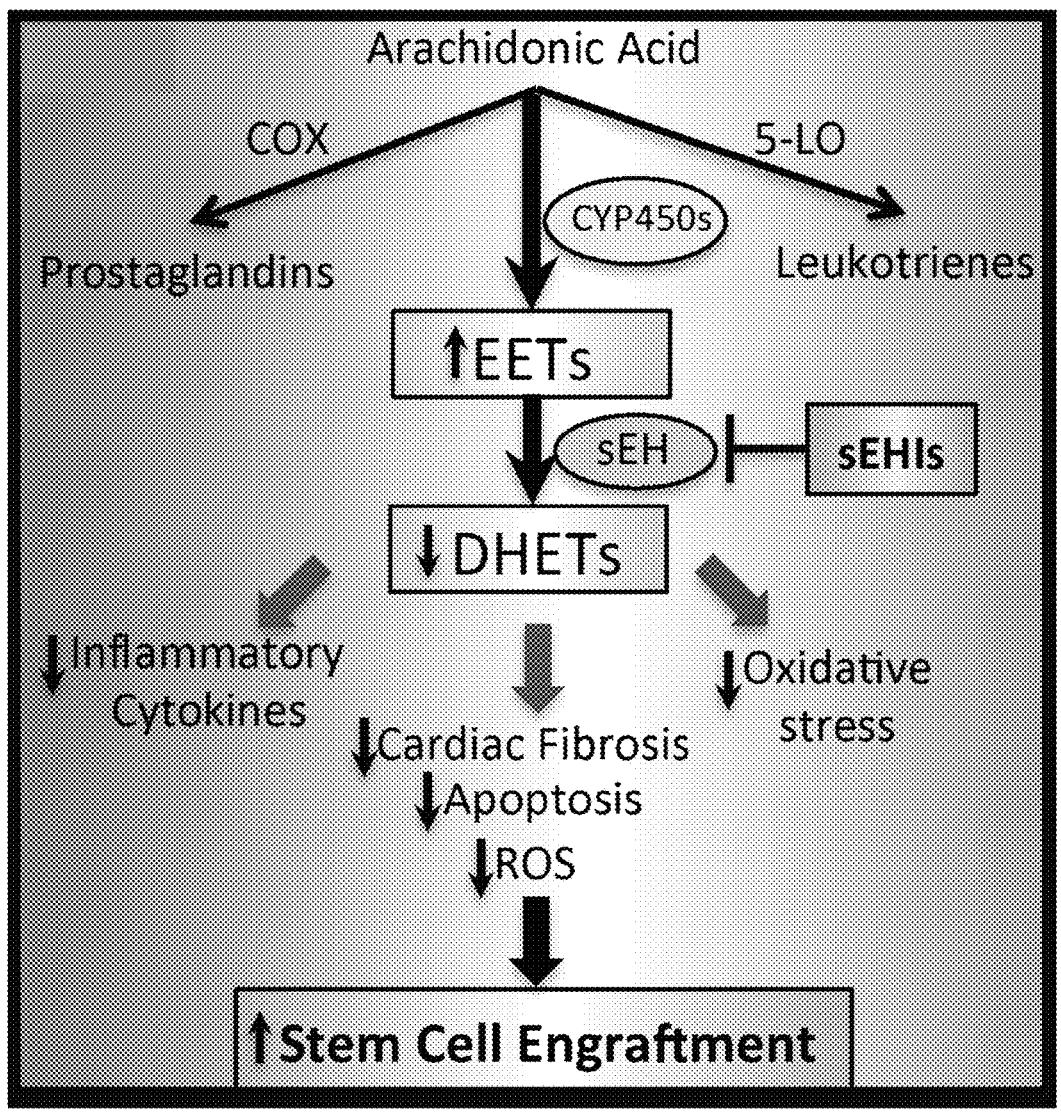
FIG. 1 illustrates arachadonic acid metabolism pathway.

Provided are methods based, in part, on the discovery that the inhibition of soluble epoxide hydrolase ("sEH"), by enhancing the biological activity of EETs with anti-inflammatory actions (22), facilitates the survival, engraftment, integration, and function of transplanted stem cells to repair injured cardiac tissue.

The data provided herein employed a clinically relevant model of myocardial infarction (MI) in mice. Human induced pluripotent stem cell-derived cardiomyocytes (hiPSC-CMs) were used as the stem cell model. However, other types of stem cells can be used as well. Suppression of inflammation and resolution of pre-existing scar tissues using co-administration of sEHIs with stem cells provides an adjuvant to cell therapy independent of cells and tissue types.

Since the CYP450 pathway is evolutionarily preserved, the methods may be exploited in other inflammatory-related diseases, serving as a paradigm shift and a rehearsal for future cell-based therapy. Thus, the innovations stem from the use of specific, novel, and potent inhibitors of inflammation to reduce and remodel scars and to promote stem cell survival, engraftment, and integration. The methods further challenge conventional approaches in the treatment of MI. The data provided herein demonstrate that these tantalizing concepts are feasible.

2. Conditions Subject to Treatment

The methods can facilitate, increase, improve and/or promote the survival, engraftment, and/or integration of transplanted stem cells in a tissue of an individual in need thereof, for any condition subject to treatment by administration of stem cells. For example, co-administration of stem cells with an agent that increases the production and/or level of cis-epoxyeicosatrienoic acids ("EETs") can facilitate, increase, improve and/or promote the survival, engraftment, and/or integration of transplanted stem cells to cardiac tissue, brain tissue, neurological tissue (e.g., central or peripheral), muscular tissue, bone tissue, renal tissue, skin, liver, pancreas, lung, inner ear, spinal cord, gingiva, or any other tissue that can be healed or repaired using stem cells.

In varying embodiments, the subject has cardiomyopathy or cardiac arrhythmia. For example, the subject may have hypertrophic cardiomyopathy, e.g., due to valvular heart disease, familial hypertrophic cardiomyopathy, dilated cardiomyopathy, myocardial infarction, or secondary to administration of an anti-cancer drug or exposure to a toxic agent. Valvular heart disease can arise from any etiology, including, e.g., secondary to rheumatic fever, myxomatous degeneration of the valve, or papillary muscle dysfunction. In varying embodiments, the subject has cardiac arrhythmia, e.g., due to atrial fibrillation, ventricular fibrillation, or ventricular tachycardia.

a. Cardiac Hypertrophy

Cardiomyocytes are terminally differentiated cells. In response to various extracellular stimuli, cardiomyocytes grow in a hypertrophic manner, an event that is characterized by enlargement of individual cell size, an increase in the content of contractile proteins such as myosin heavy chain, and expression of embryonic genes such as atrial natriuretic factor (ANF). (Chien et al., Faseb J.; 5:3037-46 (1991); Chien, Cardiologia.; 37:95-103 (1992); Chien, J Clin Invest.; 105:1339-42 (2000)) The collective result is cardiac hypertrophy, which is an adaptive and compensatory response in nature. The initial or compensated stage of hypertrophy normalizes wall stress per unit of myocardium and is thus a basic mechanism for maintaining normal chamber function. (Grossman et al, J Clin Invest.; 56:56-64 (1975)) However, this process is a double-edged sword: sustained cardiac hypertrophy will eventually lead to overt heart failure.

In most instances, heart failure is the final consequence of many underlying disease etiologies such as long-standing hypertension, coronary heart disease, valvular insufficiency, arrhythmia, viral myocarditis, and mutations in sarcomere-encoding genes. A compensatory enlargement of the myocardium, or hypertrophy, typically accompanies many of these predisposing insults and is a leading predictor for the development of more serious and life-threatening disease. Decompensated hypertrophy occurs if increased cardiac mass fails to normalize wall stress and the contractile function is not sufficient to maintain normal pump function. This is associated with clinical and pathological features of congestion.

Cardiac hypertrophy is characterized by an increase in heart-to-body weight ratio and an increase in the size of the individual cardiac myocytes, enhanced protein synthesis, and heightened organization of the sarcomere. Classically, two different hypertrophic phenotypes can be distinguished: (1) concentric hypertrophy due to pressure overload, which is characterized by parallel addition of sarcomeres and lateral growth of individual cardiomyocytes, and (2) eccentric hypertrophy due to volume overload or prior infarction, characterized by addition of sarcomeres in series and longitudinal cell growth. (Dorn et al., Circ Res.; 92:1171-5 (2003)). At the molecular level, these changes in cellular phenotype are accompanied by reinduction of the so-called fetal gene program, because patterns of gene expression mimic those seen during embryonic development. (Chien et al., Faseb J; 5:3037-46 (1991); Chien K R, Cardiologia.; 37:95-103 (1992)).

Hypertrophic transformation of the heart can be divided into three stages: (1) developing hypertrophy, in which load exceeds output, (2) compensatory hypertrophy, in which the workload/mass ratio is normalized and resting cardiac output is maintained, and (3) overt heart failure, with ventricular dilation and progressive declines in cardiac output despite continuous activation of the hypertrophic program. (Meerson F Z, Cor Vasa.; 3:161-77 (1961)). The late-phase "remodeling" process that leads to failure is associated with functional perturbations of cellular $Ca^{2+}$ homeostasis (Bers D M, Nature.; 415:198-205 (2002); Bers D M, Circ Res.; 90:14-7 (2002)) and ionic currents, (Ahmmed et al., Circ Res.; 86(5):558-70 (2000); Kaab et al., Circ Res.; 78:262-273 (1996); Kaab et al., Circulation.; 98:1383-93 (1998)) which contribute to an adverse prognosis by predisposing to ventricular dysfunction and malignant arrhythmia. Significant morphological changes include increased rates of apoptosis, (Haunstetter A and Izumo S, Circ Res.; 86:371-6 (2000)) fibrosis, and chamber dilation.

The dichotomy between adaptive and maladaptive hypertrophy has been appreciated for some time, and the mechanisms that determine how long-standing hypertrophy ultimately progresses to overt heart failure are in the process of being elucidated. One biochemical hallmark of left ventricular hypertrophy induced by pressure overload is a shift in myosin isoform from .alpha.- to .beta.-myosin heavy chains. (Delcayre C and Swynghedauw B, Pflugers Arch.; 355:39-47 (1975)). This alteration in myosin isoform expression result from transcriptionally mediated alteration in gene expression. (Boehler et al., J Biol. Chem.; 267:12979-12985 (1992)). Various lines of evidence suggest a decrease in the expression of the sarcoplasmic reticulum $Ca^{2+}$-cycling protein, $Ca^{2+}$ ATPase during the development of heart failure in several animal models, including humans with end-stage congestive heart failure, even though no changes can be detected during the compensated hypertrophied stage. (Kiss et al., Circ Res.; 77:759-764 (1995); Feldman et al., Circulation.; 75:331-9 (1987); Arai et al, Circ Res.; 72:463-469 (1993)). These changes are associated with a decrease in sarcoplasmic reticulum $Ca^{2+}$ transport. In addition, there are alterations in the level of phospholamban, sarcoplasmic reticulum $Ca^{2+}$-release channels and in $Ca^{2+}$ cycling proteins in the myofibrils and sarcolemma in different animal models with heart failure. (de la Bastie et al., Circ Res.; 66:554-564 (1990); Mercadier et al., J Clin Invest.; 85:305-309 (1990)). These studies suggest that critical components of the $Ca^{2+}$ cycling system may be responsible, in part, for the transitions between compensated pressure-overload hypertrophy and congestive heart failure.

Hypertrophy that occurs as a consequence of pressure overload is termed "compensatory" on the premise that it facilitates ejection performance by normalizing systolic wall stress. Recent experimental results, however, call into question the necessity of normalization of wall stress that results from hypertrophic growth of the heart. These findings, largely from studies in genetically engineered mice, raise the prospect of modulating hypertrophic growth of the myocardium to afford clinical benefit without provoking hemodynamic compromise. (Frey et al., supra, Dorn and Molkentin, supra; Frey et al., Circulation.; 109:1580-9 (2004)).

It is generally accepted that cardiac hypertrophy can be adaptive in some situations, for example, in athletes. However, it is less clear if a hypertrophic response to pathological situations, such as valvular heart disease, chronic arterial hypertension or a myocardial infarction, is initially a compensatory response and later becomes maladaptive or if this type of myocardial growth is detrimental from the outset.

It has been demonstrated that these different types of cardiac hypertrophy differ both at the morphological as well as the molecular level. Exercise-induced cardiac hypertrophy is generally not accompanied by an accumulation of collagen in the myocardium and usually does not exceed a modest increase in ventricular wall thickness. In addition, there are significantly differences in the expression levels for several hypertrophic genes, such as BNP or ET-1. Further, the isoform expression of α-/β-MHCs is regulated in opposite directions in exercise versus pressure overload-induced cardiac hypertrophy. However, some hypertrophic pathways, such as calcineurin-dependent signaling, appear to be activated in both pathological and physiological exercise-induced hypertrophy, as demonstrated by the finding that the calcineurin inhibitor can attenuate both phenotypes. Taken together, these data indicate that exercise-associated (physiologic) versus pathologic hypertrophy differ at the molecular level, but this does not exclude the possibility that certain pathways may be involved in all phenotypes of cardiac hypertrophy.

Since adult cardiomyocytes are terminally differentiated cells, many of the same intracellular signaling pathways that regulate proliferation in cancer cells or immune cells instead regulate hypertrophic growth of cardiomyocytes. The hypertrophic growth can be initiated by endocrine, paracrine, and autocrine factors that stimulate a wide array of membrane-bound receptors. Their activation results in the triggering of multiple cytoplasmic signal transduction cascades, which ultimately affects nuclear factors and the regulation of gene expression. It has previously been documented that no single intracellular transduction cascade regulates cardiomyocyte hypertrophy in isolation, but instead each pathway operates as an integrated component between interdependent and cross-talking networks. Therefore, blockade of specific intracellular signaling pathways in the heart can dramatically affect the entire hypertrophic response and effectively decrease cardiac hypertrophy. Furthermore, specific activation of a number of discrete signal transduction pathways may be sufficient to activate the entire hypertrophic response through effects on other cross-talking signaling networks.

b. Valvular Heart Disease

The heart has four valves: the mitral valve (the only valve with two flaps), the tricuspid, with three differently sized flaps, the aortic valve, which opens to allow blood from the heart into the aorta, and the pulmonary valve. A number of disorders affecting the valves can result in increased pressure in the chambers of the heart, which in turn can result in cardiac hypertrophy. These conditions include mitral valve stenosis, mitral valve insufficiency, aortic valve insufficiency, aortic valve stenosis, and tricuspid valve insufficiency. Several of these conditions occur in persons who had undiagnosed or incompletely treated rheumatic fever as a child. Rheumatic fever occurs most often in children who have a streptococcal throat infection ("strep throat"), and can result in mitral stenosis, tricuspid stenosis, aortic insufficiency, aortic stenosis, multivalvular involvement or, less commonly, pulmonic stenosis. Unlike stenosis of blood vessels, which is typically caused by a build-up of lipids and cells on the interior of the vessel lumen, stenosis of heart valves is typically due to fusing of the flaps, to a build-up of calcium on the flap, causing it to harden, to a congenital deformity, a weakening of valve tissue ("myxomatous degeneration"), or use of certain medicines, such as fenfluramine and dexfenfluramine.

3. Preparation and Administration of Stem Cells

The administered stem cells will be appropriate to the tissue being targeted and treated or repaired. In varying embodiments, the stem cells are multipotent or pluripotent, and can be isolated or induced. In varying embodiments, the stem cells are mesenchymal stem cells, or stem cells derived or induced from the tissue of interest (e.g., muscle tissue, particularly cardiac muscle tissue, nerve tissue). In varying embodiments, the stem cells are isolated, derived or induced from myocyte cells. In varying embodiments, the stem cells are isolated, derived or induced from cardiomyocyte cells. In varying embodiments, are isolated, derived or induced from cardiomyocytes or cardiac progenitor cells derived from multipotent stem cells, cardiomyocytes or cardiac progenitor cells derived from pluripotent stem cells, cardiomyocytes or cardiac progenitor cells derived from induced pluripotent stem cells, adult cardiac progenitor cells or cardiac stem cells. Isolation, derivation and/or production of cardiac progenitor cells (Sca-1+/CD31− cells) and cardiac stem cells is known in the art, as published in, e.g., Wang, et al., *PLoS One.* 2014 June 11; 9(6):e95247; Pagliari, et al., *Front Physiol.* 2014 Jun. 3; 5:210; Beltrami, et al., *Cell.* 2003 Sep. 19; 114(6):763-76; Bolli, et al., *Lancet.* 2011 Nov. 26; 378(9806):1847-57; Chugh, et al., *Circulation.* 2012 Sep. 11; 126(11 Suppl 1):554-64; Makkar, et al., *Lancet.* 2012 Mar. 10; 379(9819):895-904; Malliaras, et al., *J Am Coll Cardiol.* 2014 Jan. 21; 63(2): 110-22; Delewi, *Heart.* 2013 February; 99(4):225-32; Clifford, et al., *Cochrane Database Syst Rev.* 2012 Feb. 15; 2:CD006536; Dan, et al., *Am J Stem*

Cells. 2014 Mar. 13; 3(1):37-45; Wickham, et al., *J Biomed Mater Res B Appl Biomater.* 2014 Mar. 24; and other references cited herein.

a. Mesenchymal Stem Cells

In varying embodiments, the stem cells are mesenchymal stem cells. The bone marrow and adipose tissue of an adult mammal is a repository of mesenchymal stem cells (MSCs). Bone marrow MSCs are self-renewing, clonal precursors of non-hematopoietic tissues. MSCs for use in the present methods can be isolated from a variety of tissues, including bone marrow, muscle, fat (i.e., adipose), liver, dermis, gingiva and periodontal ligament, using techniques known in the art. Depending on the stimulus and the culture conditions employed, these cells can form bone, cartilage, tendon/ligament, muscle, marrow, adipose, and other connective tissues.

In some embodiments, the MSCs are derived from adipose tissue. Adipose-derived MSCs (AdMSCs) can be obtained from either autologous (self) and allogeneic (non-self) sources. The use of allogeneic MSCs in patients is possible due to their low immunogenicity. However, autologous adMSCs are non-immunogeneic and considered to be safe in people and animals. AdMSCs can be administered either systemically (e.g., intravenous or intraarterially) or locally (e.g., directly to cardiac tissue, e.g., via the coronary artery) in the treatment of disorders. MSCs can be generated more efficiently and rapidly from adipose tissue than from bone marrow. Fat- or adipose-derived MSCs are present in higher number and have a significantly higher proliferation rate then bone-marrow derived MSCs.

Generally, the MSCs useful for administration express on their cell surface CD44, CD90 and CD105 and do not express on their cell surface CD4, CD34, CD45, CD80, CD86 or MHC-II. In various embodiments, the MSCs are adipose-derived mesenchymal stem cells (Ad-MSC). Ad-MSCs can be characterized by the surface expression of CD5, CD44, CD90 (Thy-1) and CD105; and by the non-expression of CD3, CD4, CD18, CD34, CD45, CD49d, CD80, CD86 and MHC class II. In other embodiments, the MSCs are derived from a non-adipose tissue, for example, bone marrow, liver, periodontal ligament, gingiva and/or dermal tissues. In some embodiments, the MSCs are non-hematopoietic stem cells derived from bone marrow (e.g., do not express CD34 or CD45). Cell surface markers of cardiac progenitor cells can include cKit, P-glycoprotein (a member of the multidrug resistance protein family), and Sca-1 (stem cell antigen 1), Sca-1-like, ISL LIM homeobox 1 (ISL1), and/or kinase insert domain receptor (a type III receptor tyrosine kinase) (KDR). See, e.g., Barile, et al., *Nat Clin Pract Cardiovasc Med.* 2007 February; 4 Suppl 1:S9-S14.

As appropriate, the MSCs can be autologous (i.e., from the same subject), syngeneic (i.e., from a subject having an identical or closely similar genetic makeup); allogeneic (i.e., from a subject of the same species) or xenogeneic to the subject (i.e., from a subject of a different species).

In various embodiments, the MSCs may be altered to enhance the viability of engrafted or transplanted cells. For example, the MSCs can be engineered to overexpress or to constitutively express Akt. See, e.g., U.S. Patent Publication No. 2011/0091430.

b. Preparation

Tissue comprising mesenchymal stem cells (MSCs) is obtained and processed. As appropriate the tissue can be adipose, bone marrow, periodontal ligament, gingiva, muscle, liver or dermis. The obtained MSCs can be autologous, syngeneic, allogeneic or xenogeneic to the subject mammal. The tissue is processed to isolate the MSCs such that they can be cultured in vitro. Solid tissues can be minced and digested with a proteinase (e.g., collagenase), as appropriate. In varying embodiments, the isolated MSCs can be cultured in vitro for at least 1 passage, e.g., from about 2 passages to about 8 passages, e.g. for 2, 3, 4, 5, 6, 7, 8 passages, as appropriate. At least 24 hours prior to injection into the subject, e.g., 24, 36 or 48 hours prior to injection, the cultured MSCs are washed and then cultured in media comprising serum of the same species of the subject mammal (e.g., autologous, syngeneic and/or allogeneic serum) and in the absence of serum xenogeneic to the subject mammal to wash out serum proteins allogeneic to the subject mammal in order to avoid or minimize the risk of a potential transfusion reaction. For example, the present MSCs are substantially free of bovine and/or equine serum proteins prior to injection.

Prior to injection or engraftment into the subject mammal, the MSCs are rinsed and resuspended in a serum-free isotonic buffered solution (e.g., phosphate-buffered saline, 0.9% sodium chloride, lactated Ringer's solution (LRS), Hank's Balanced Salt Solution (HBSS), Earle's Balanced Salt Solution (EBSS), etc.).

In varying embodiments, the MSCs administered to the subject are fresh (i.e., not frozen) and viable. In varying embodiments, the MSCs have been cultured in vitro for one or more passages prior to injection, so the administered MSCs have never been frozen. The MSCs are evaluated for viability prior to administration. In varying embodiments, the population of administered MSCs are at least about 50% viable, e.g., at least about 55%, 60%, 65%, 70%, 75%, 80%, 85%, 90%, 95%, 98%, 99%, 100% viable.

c. Administration of Stem Cells

The stem cells can be administered by any appropriate route. In various embodiments, the stem cells are systemically administered, e.g., intravenously, intra-arterially, or administered directly to the tissue of interest for treatment or repair.

In some embodiments, the stem cells are administered locally, e.g., directly to cardiac tissue. As appropriate, the stem cells can be engrafted or transplanted into and/or around the tissue of interest, e.g., cardiac tissues. When engrafted or transplanted into and/or in the vicinity of one or more tissues of interest (e.g., cardiac tissues), the stem cells are administered within or within sufficient proximity of inflamed or damaged lesions in tissue to mitigate and/or reverse of damage and/or destruction of the tissue. For example, the stem cells are engrafted or transplanted into or within sufficient proximity to the tissue of interest to prevent, reduce or inhibit damage and/or destruction to the tissues.

As appropriate, injections of stem cells can be done after local anesthetics (e.g., lidocaine, bupivacaine) have been administered. It is also possible to inject the stem cells in conjunction with local anesthetics added to the cell suspension. Injections can also be made with the subject under general anesthesia with or without the use of local anesthetic agents (e.g., lidocaine).

In various embodiments, engraftment or transplantation of the stem cells can be facilitated using a matrix or caged depot. For example, the stem cells can be engrafted or transplanted in a "caged cell" delivery device wherein the cells are integrated into a biocompatible and/or biologically inert matrix (e.g. a hydrogel or other polymer or any device) that restricts cell movement while allowing the cells to remain viable. Synthetic extracellular matrix and other biocompatible vehicles for delivery, retention, growth, and differentiation of stem cells are known in the art and find use in the present methods. See, e.g., Prestwich, *J Control Release*. 2011 Apr. 14, PMID 21513749; Perale, et al., *Int J Artif Organs*. (2011) 34(3):295-303; Suri, et al., *Tissue Eng Part A*. (2010) 16(5):1703-16; Khetan, et al., *J Vis Exp*. (2009) October 26; (32). pii: 1590; Salinas, et al., *J Dent Res*. (2009) 88(8):681-92; Schmidt, et al., *J Biomed Mater Res A*. (2008) 87(4):1113-22 and Xin, et al., *Biomaterials* (2007) 28:316-325.

As appropriate or desired, the engrafted or transplanted stem cells can be modified to facilitate retention of the stem cells at the region of interest or the region of delivery. In other embodiments, the region of interest for engraftment or transplantation of the cells is modified in order to facilitate retention of the stem cells at the region of interest or the region of delivery. In one embodiment, this can be accomplished by introducing stromal cell derived factor-1 (SDF-1) into the region of interest, e.g., using a linkage chemistry or integrated biodegradable matrix (e.g., Poly(D,L-lactide-coglycolide (PLGA) beads) that would provide a tunable temporal presence of the desired ligand up to several weeks. Stem cells bind to the immobilized SDF-1, thereby facilitating the retention of stem cells that are delivered to the region of interest for engraftment or transplantation. In other embodiments, integrating cyclic arginine-glycine-aspartic acid peptide into the region of interest can facilitate increased stem cell binding and retention at the region of interest for engraftment or transplantation. See, e.g., Ratliff, et al., *Am J Pathol*. (2010) 177(2):873-83.

In some embodiments, at least about 1 million stem cells/kg subject are administered or engrafted, e.g., at least about 2 million, 2.5 million, 3 million, 3.5 million, 4 million, 5 million, 6 million, 7 million, 8 million, 9 million or 10 million stem cells/kg subject are administered. In varying embodiments, about 1 million to about 10 million stem cells/kg subject, e.g., about 2 million to about 8 million stem cells/kg are administered or grafted.

In varying embodiments, at least about 5 million stem cells are administered or engrafted, e.g., at least about 10 million, 15 million, 20 million, 25 million, 30 million, 35 million, 40 million, 45 million, 50 million, 55 million, 60 million, 65 million, 70 million, 75 million, 80 million, 85 million, 90 million, 95 million or 100 million stem cells are administered or engrafted. In varying embodiments, about 5 million to about 100 million stem cells are administered or engrafted, e.g., about 10 million to about 80 million stem cells are administered or engrafted. In varying embodiments, at least about 50 million stem cells are administered or engrafted, e.g., at least about 100 million, 150 million, 200 million, 250 million, 300 million, 350 million, 400 million, 450 million, 500 million, 550 million, 600 million, 650 million, 700 million, 750 million, 800 million, 850 million, 900 million, 950 million or 1 billion stem cells are administered or engrafted.

In varying embodiments, the stem cells are administered, e.g., intravenously, at a rate of about 1 million to about 10 million cells per minute, e.g., at a rate of about 2 million to about 4 million cells per minute, e.g., at a rate of about 2.5 million to about 3.5 million cells per minute.

A regime of treatment or prevention may involve one or multiple injections. For example, stem cells may be administered to the subject 1, 2, 3, 4, 5, 6, 7, 8, 9, 10, or more times, as appropriate. Subsequent administrations of stem cells may be administered systemically or locally. If administered locally, multiple injections of stem cells may be administered to the same or different locations. Multiple injections of stem cells can be administered daily, weekly, bi-weekly, monthly, bi-monthly, every 3, 4, 5, or 6 months, or annually, or more or less often, as needed by the subject. The frequency of administration of the stem cells can change over a course of treatment, e.g., depending on how well the engrafted or transplanted stem cells establish themselves at the site of administration and the responsiveness of the subject. The stem cells may be administered multiple times over a regime course of several weeks, several months, several years, or for the remainder of the life of the subject, as needed or appropriate.

The total amount of cells that are envisioned for use depend upon the desired effect, patient state, and the like, and may be determined by one skilled within the art. Dosages for any one patient depends upon many factors, including the patient's species, size, body surface area, age, the particular stem cells to be administered, sex, scheduling and route of administration, general health, and other drugs being administered concurrently.

4. Agents that Increase the Production and/or Level of Epoxygenated Fatty Acids

Agents that increase epoxygenated fatty acids include epoxygenated fatty acids (e.g., including EETs), and inhibitors of soluble epoxide hydrolase (sEH).

a. Inhibitors of Soluble Epoxide Hydrolase (sEH)

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. In various embodiments, the urea, carbamate or amide pharmacophore is covalently bound to both an adamantane and to a 12 carbon chain dodecane. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A., 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH. Thus, isomers of adamantyl dodecyl urea are preferred inhibitors. It is further expected that N, N'-dodecyl-cyclohexyl urea (DCU), and other inhibitors of sEH, and particularly dodecanoic acid ester derivatives of urea, are suitable for use in the methods. Preferred inhibitors include:

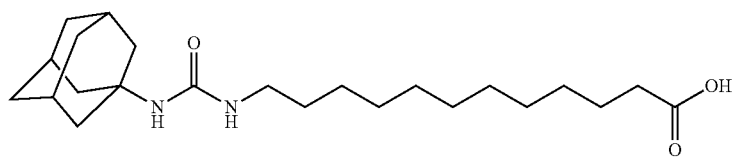

12-(3-Adamantan-1-yl-ureido)dodecanoic acid (AUDA),

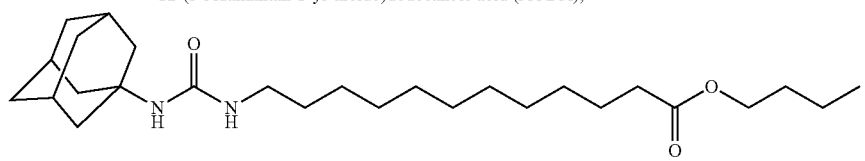

12-(3-Adamantan-1-yl-ureido)dodecanoic acid butyl ester (AUDA-BE),

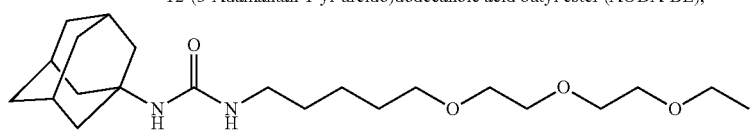

Adamantan-1-yl-3-{5-[2-(2-ethoxy)ethoxy]pentyl}urea
(compound 950, also referred to herein as "AEPU"), and Another preferred group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

$IC_{50}$ values for selected alkylpiperidine-based sEH inhibitors against human sEH

| R: | | n = 0 | | n = 1 | |
|---|---|---|---|---|---|
| | | Compound | $IC_{50}$ (μM)[a] | Compound | $IC_{50}$ (μM)[a] |
| | H | I | 0.30 | II | 4.2 |
| | ethyl | 3a | 3.8 | 4a | 3.9 |
| | propyl | 3b | 0.81 | 4b | 2.6 |
| | butyl | 3c | 1.2 | 4c | 0.61 |
| | benzyl | 3d | 0.01 | 4d | 0.11 |

[a] As determined via a kinetic fluorescent assay.

TABLE 2

| sEH inhibitors | | |
|---|---|---|
| Structure | Name | sEHi # |
| [structure] | 3-(4-chlorophenyl)-1-(3,4-dichlorphenyl)urea or 3,4,4'-trichlorocarbanilide | 295 (TCC) |
| [structure] | 12-(3-adamantan-1-yl-ureido) dodecanoic acid | 700 (AUDA) |
| [structure] | 1-adamantanyl-3-{5-[2-(2-ethoxyethoxy)ethoxy]pentyl]}urea | 950 (AEPU) |
| [structure] | 1-(1-acetypiperidin-4-yl)-3-adamantanylurea | 1153 (APAU) |
| [structure] | trans-4-[4-(3-Adamantan-1-yl-ureido)-cyclohexyloxy]-benzoic acid | 1471 (tAUCB) |
| [structure] | 1-trifluoromethoxyphenyl-3-(1-acetylpiperidin-4-yl) urea | 1555 (TPAU) |
| [structure] | cis-4-[4-(3-Adamantan-1-yl-ureido)-cyclohexyloxy]-benzoic acid | 1686 (cAUCB) |
| [structure] | 1-(1-methylsulfonyl-piperidin-4-yl)-3-(4-trifluoromethoxy-phenyl)-urea | 1709 (TUPS) |

TABLE 2-continued sEH inhibitors

| Structure | Name | sEHi # |
|---|---|---|
| 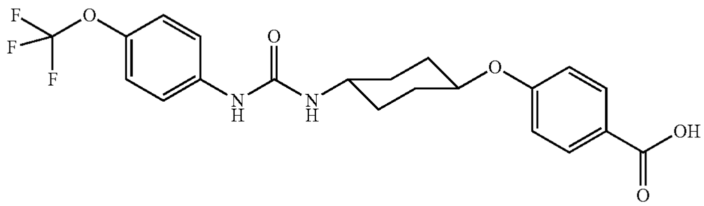 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) |
| 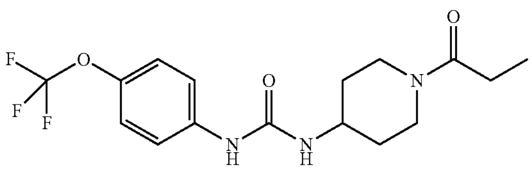 [SMILES: CCC(=O)N1CCC(NC(=O)Nc2ccc(OC(F)(F)F)cc2)CC1] | 1-trifluoromethoxyphenyl-3-(1-propionylpiperidin-4-yl) urea | 1770 (TPPU) |
| 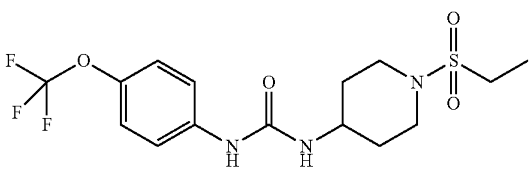 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) |
| | 1-(1-(cyclopropanecarbonyl)piperidin-4-yl)-3-(4-(trifluoromethoxy)phenyl)urea | 2214 (CPTU) |
| 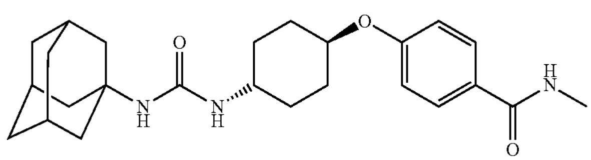 | trans-N-methyl-4-[4-(3-Adamantan-1-yl-ureido)-cyclohexyloxy]-benzamide | 2225 (tMAUCB) |
| 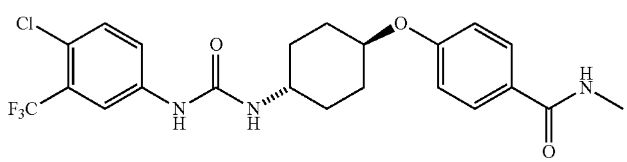 | trans-N-methyl-4-[4-((3-trifluoromethyl-4-chlorophenyl)-ureido)-cyclohexyloxy]-benzamide | 2226 (tMTCUCB) |
| 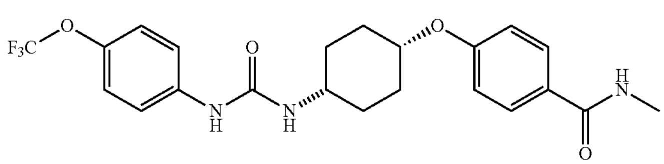 | cis-N-methyl-4-{4-[3-(4-trifluoromethoxy-phenyl)-ureido]-cyclohexyloxy}-benzamide | 2228 (cMTUCB) |
| 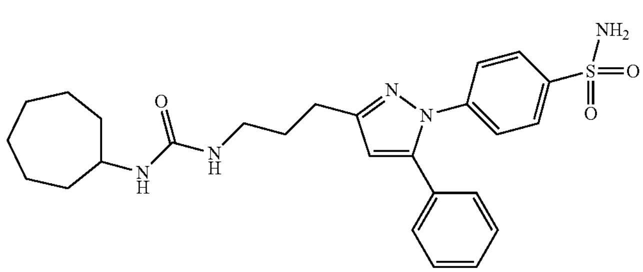 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) |

A number of other sEH inhibitors which can be used in the methods and compositions are set forth in co-owned applications PCT/US2013/024396, PCT/US2012/025074, PCT/US2011/064474, PCT/US2011/022901, PCT/US2008/

072199, PCT/US2007/006412, PCT/US2005/038282, PCT/US2005/08765, PCT/US2004/010298 and U.S. Published Patent Application Publication Nos: 2014/0088156, 2014/0038923, 2013/0274476, 2013/0143925, 2013/0137726, 2011/0098322, 2005/0026844, each of which is hereby incorporated herein by reference in its entirety for all purposes.

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent). Two preferred classes of sEH inhibitors are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty sEH inhibitors of Formula 2, which were shown to inhibit human sEH at concentrations as low as 0.1 µM. Any particular sEH inhibitor can readily be tested to determine whether it will work in the methods by standard assays. Esters and salts of the various compounds discussed above or in the cited patents, for example, can be readily tested by these assays for their use in the methods.

As noted above, chalcone oxides can serve as an alternate substrate for the enzyme. While chalcone oxides have half-lives which depend in part on the particular structure, as a group the chalcone oxides tend to have relatively short half-lives (a drug's half-life is usually defined as the time for the concentration of the drug to drop to half its original value. See, e.g., Thomas, G., Medicinal Chemistry: an introduction, John Wiley & Sons Ltd. (West Sussex, England, 2000)). Since the various uses contemplate inhibition of sEH over differing periods of time which can be measured in days, weeks, or months, chalcone oxides, and other inhibitors which have a half-life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half-lives although, for inhibitors with a relatively short half-life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28; 54(8):3037-50.

Preferably, the inhibitor inhibits sEH without also significantly inhibiting microsomal epoxide hydrolase ("mEH"). Preferably, at concentrations of 100 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 100 µM. Inhibitors with $IC_{50}$s of less than 100 M are preferred, with $IC_{50}$s of less than 75 µM being more preferred and, in order of increasing preference, an $IC_{50}$ of 50 µM, 40 µM, 30 µM, 25 µM, 20 µM, 15 µM, 10 µM, 5 µM, 3 µM, 2 µM, 1 µM, 100 nM, 10 nM, 1.0 nM, or even less, being still more preferred. Assays for determining sEH activity are known in the art and described elsewhere herein. The $IC_{50}$ determination of the inhibitor can be made with respect to an sEH enzyme from the species subject to treatment (e.g., the subject receiving the inhibitor of sEH).

b. Cis-epoxyeicosatrienoic Acids ("EETs")

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half-life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHI to provide a therapeutic effect. Moreover, EETs, if not exposed to acidic conditions or to sEH are stable and can withstand reasonable storage, handling and administration.

In short, sEHI, EETs, or co-administration of sEHIs and of EETs, can be used in the methods of the present invention. In some embodiments, one or more EETs are administered to the patient without also administering an sEHI. In some embodiments, one or more EETs are administered shortly before or concurrently with administration of an sEH inhibitor to slow hydrolysis of the EET or EETs. In some embodiments, one or more EETs are administered after administration of an sEH inhibitor, but before the level of the sEHI has diminished below a level effective to slow the hydrolysis of the EETs.

EETs useful in the methods of the present invention include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

If desired, EETs, analogs, or derivatives that retain activity can be used in place of or in combination with unmodified EETs. Liao and Zeldin, supra, define EET analogs as compounds with structural substitutions or alterations in an EET, and include structural analogs in which one or more EET olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, urea, amide, carbamate, difluorocycloprane, or carbonyl, while in others, the carboxylic acid moiety is stabilized by blocking beta oxidation or is replaced with a commonly used mimic, such as a nitrogen heterocycle, a sulfonamide, or another polar functionality. In preferred forms, the analogs or derivatives are relatively stable as compared to an unmodified EET because they are more resistant than an unmodified EET to sEH and to chemical breakdown. "Relatively stable" means the rate of hydrolysis by sEH is at least 25% less than the hydrolysis of the unmodified EET in a hydrolysis assay, and more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. Whether or not a particular EET analog or derivative has the biological activity of the unmodified EET can be readily determined by using it in standard assays, such as radio-ligand competition assays to measure binding to the relevant receptor. As mentioned in the Definition section, above, for convenience of reference, the term "EETs" as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice.

c. Assays for Epoxide Hydrolase Activity

Any of a number of standard assays for determining epoxide hydrolase activity can be used to determine inhibition of sEH. For example, suitable assays are described in Gill., et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al. , In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

d. Other Means of Inhibiting sEH Activity

Other means of inhibiting sEH activity or gene expression can also be used in the methods. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and microRNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the nonspecific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, siRNA were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). An exemplary amino acid sequence of human sEH (GenBank Accession No. L05779 or AAA02756; SEQ ID NO: 1) and an exemplary nucleotide sequence encoding that amino acid sequence (GenBank Accession No. L05779; SEQ ID NO:2) are set forth in U.S. Pat. No. 5,445,956. The nucleic acid sequence of human sEH is also published as GenBank Accession No. NM_001979.4 (SEQ ID NO: 39); the amino acid sequence of human sEH is also published as GenBank Accession No. NP_001970.2 (SEQ ID NO: 40).

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

1) Target:
CAGTGTTCATTGGCCATGACTGG (SEQ ID NO: 3)

Sense-siRNA:
5'-GUGUUCAUUGGCCAUGACUTT-3' (SEQ ID NO: 4)

Antisense-siRNA:
5'-AGUCAUGGCCAAUGAACACTT-3' (SEQ ID NO: 5)

2) Target:
GAAAGGCTATGGAGAGTCATCTG (SEQ ID NO: 6)

Sense-siRNA:
5'-AAGGCUAUGGAGAGUCAUCTT-3' (SEQ ID NO: 7)

Antisense-siRNA:
5'-GAUGACUCUCCAUAGCCUUTT-3' (SEQ ID NO: 8)

3) Target
AAAGGCTATGGAGAGTCATCTGC (SEQ ID NO: 9)

Sense-siRNA:
5'-AGGCUAUGGAGAGUCAUCUTT-3' (SEQ ID NO: 10)

Antisense-siRNA:
5'-AGAUGACUCUCCAUAGCCUTT-3' (SEQ ID NO: 11)

4) Target:
CAAGCAGTGTTCATTGGCCATGA (SEQ ID NO: 12)

Sense-siRNA:
5'-AGCAGUGUUCAUUGGCCAUTT-3' (SEQ ID NO: 13)

Antisense-siRNA:
5'-AUGGCCAAUGAACACUGCUTT-3' (SEQ ID NO: 14)

5) Target:
CAGCACATGGAGGACTGGATTCC (SEQ ID NO: 15)

Sense-siRNA:
5'-GCACAUGGAGGACUGGAUUTT-3' (SEQ ID NO: 16)

Antisense-siRNA:
5'-AAUCCAGUCCUCCAUGUGCTT-3' (SEQ ID NO: 17)

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

```
1) Target:
                                    (SEQ ID NO: 19)
CAGTGTTCATTGGCCATGACTGG Sense strand:
                                    (SEQ ID NO: 20)
5'-GATCCCCGTGTTCATTGGCCATGACTTTCAA
GAGAAGTCATGGCCAATGAACACTTTTT-3'

Antisense strand:
                                    (SEQ ID NO: 21)
5'-AGCTAAAAAGTGTTCATTGGCCATGACTTCTCTT
GAAAGTCATGGCCAATGAACACGGG-3'

2) Target:
                                    (SEQ ID NO: 22)
GAAAGGCTATGGAGAGTCATCTG Sense strand:
                                    (SEQ ID NO: 23)
5'-GATCCCCAAGGCTATGGAGAGTCATCTTCAAGAGAGA
TGACTCTCCATAGCCTTTTTTT-3'

Antisense strand:
                                    (SEQ ID NO: 24)
5'-AGCTAAAAAAGGCTATGGAGAGTCATCTCTCTTGAA
GATGACTCTCCATAGCCTTGGG-3'

3) Target:
                                    (SEQ ID NO: 25)
AAAGGCTATGGAGAGTCATCTGC Sense strand:
                                    (SEQ ID NO: 26)
5'-GATCCCCAGGCTATGGAGAGTCATCTTTCAAGAGAAG
ATGACTCTCCATAGCCTTTTTT-3'

Antisense strand:
                                    (SEQ ID NO: 27)
5'-
AGCTAAAAAAGGCTATGGAGAGTCATCATCTCTTGAAAGATGACT
CTCCATAGCCTGGG-3'

4) Target:
                                    (SEQ ID NO: 28)
CAAGCAGTGTTCATTGGCCATGA Sense strand:
                                    (SEQ ID NO: 29)
5'-GATCCCCAGCAGTGTTCATTGGCCATTTCAAGAGAATG
GCCAATGAACACTGCTTTTTT-3'

Antisense strand:
                                    (SEQ ID NO: 30)
5'-AGCTAAAAAAGCAGTGTTCATTGGCCATTCTCTTGAAATG
GCCAATGAACACTGCTGGG-3'

5) Target:
                                    (SEQ ID NO: 31)
CAGCACATGGAGGACTGGATTCC Sense strand
                                    (SEQ ID NO: 32)
5'-GATCCCCGCACATGGAGGACTGGATTTTCAAGAGAAATC
CAGTCCTCCATGTGCTTTTT-3'
```

```
Antisense strand:
                                    (SEQ ID NO: 33)
5'-AGCTAAAAAGCACATGGAGGACTGGATTTCTCTTGAAAA
TCCAGTCCTCCATGTGCGGG-3'
```

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program found on the worldwide web "biotools.idtdna.com/antisense/Anti-Sense.aspx", which will provide appropriate antisense sequences for nucleic acid sequences up to 10,000 nucleotides in length. Using this program with the sEH gene provides the following exemplar sequences:

```
1)
                                    (SEQ ID NO: 34)
UGUCCAGUGCCCACAGUCCU 2)
                                    (SEQ ID NO: 35)
UUCCCACCUGACACGACUCU 3)
                                    (SEQ ID NO: 36)
GUUCAGCCUCAGCCACUCCU 4)
                                    (SEQ ID NO: 37)
AGUCCUCCCGCUUCACAGA 5)
                                    (SEQ ID NO: 38)
GCCCACUUCCAGUUCCUUUCC
```

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand are transcribed and act as an antisense oligonucleotide.

It are appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced in mammals without eliciting an immune response by encapsulating them in nanoparticles of cyclodextrin. Information on this method can be found on the worldwide web at "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11): 4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

e. Epoxygenated Fatty Acids

In some embodiments, an epoxygenated fatty acid is administered as an agent that increases epoxygenated fatty acids. Illustrative epoxygenated fatty acids include epoxides of linoleic acid, eicosapentaenoic acid ("EPA") and docosahexaenoic acid ("DHA").

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100: 1340-1346 (2002). The paper did not identify the mechanism of action, nor the agents responsible for this relief.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

As mentioned, it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, increasing the levels of epoxides of EPA, of DHA, or of both, will act to reduce pain and inflammation, and symptoms associated with diabetes and metabolic syndromes, in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHI. However, the endogenous production of these epoxides is low and usually occurs in relatively special circumstances, such as the resolution of inflammation. Our expectation is that administering these epoxides from exogenous sources will aid in the resolution of inflammation and in reducing pain, as well as with symptoms of diabetes and metabolic syndromes. It is further beneficial with pain or inflammation to inhibit sEH with sEHI to reduce hydrolysis of these epoxides, thereby maintaining them at relatively high levels.

EPA has five unsaturated bonds, and thus five positions at which epoxides can be formed, while DHA has six. The epoxides of EPA are typically abbreviated and referred to generically as "EpETEs", while the epoxides of DHA are typically abbreviated and referred to generically as "EpDPEs". The specific regioisomers of the epoxides of each fatty acid are set forth in the following Table:

TABLE 3

Regioisomers of Eicosapentaenoic acid ("EPA") epoxides:

1. Formal name: (±)5(6)-epoxy-8Z,11Z,14Z,17Z-eicosatetraenoic acid,
    Synonym 5(6)-epoxy Eicosatetraenoic acid
    Abbreviation 5(6)-EpETE
2. Formal name: (±)8(9)-epoxy-5Z,11Z,14Z,17Z-eicosatetraenoic acid,
    Synonym 8(9)-epoxy Eicosatetraenoic acid
    Abbreviation 8(9)-EpETE
3. Formal name: (±)11(12)-epoxy-5Z,8Z,14Z,17Z-eicosatetraenoic acid,
    Synonym 11(12)-epoxy Eicosatetraenoic acid
    Abbreviation 11(12)-EpETE
4. Formal name: (±)14(15)-epoxy-5Z,8Z,11Z,17Z-eicosatetraenoic acid,
    Synonym 14(15)-epoxy Eicosatetraenoic acid
    Abbreviation 14(15)-EpETE
5. Formal name: (±)17(18)-epoxy-5Z,8Z,11Z,14Z-eicosatetraenoic acid,
    Synonym 17(18)-epoxy Eicosatetraenoic acid
    Abbreviation 17(18)-EpETE Regioisomers of Docosahexaenoic acid ("DHA") epoxides:
1. Formal name: (±) 4(5)-epoxy-7Z,10Z,13Z,16Z,19Z-docosapentaenoic acid,
    Synonym 4(5)-epoxy Docosapentaenoic acid
    Abbreviation 4(5)-EpDPE
2. Formal name: (±) 7(8)-epoxy-4Z,10Z,13Z,16Z,19Z-docosapentaenoic acid,
    Synonym 7(8)-epoxy Docosapentaenoic acid
    Abbreviation 7(8)-EpDPE
3. Formal name: (±)10(11)-epoxy-4Z,7Z,13Z,16Z,19Z-docosapentaenoic acid,
    Synonym 10(11)-epoxy Docosapentaenoic acid
    Abbreviation 10(11)-EpDPE
4. Formal name: (±)13(14)-epoxy-4Z,7Z,10Z,16Z,19Z-docosapentaenoic acid,
    Synonym 13(14)-epoxy Docosapentaenoic acid
    Abbreviation 13(14)-EpDPE
5. Formal name: (±) 16(17)-epoxy-4Z,7Z,10Z,13Z,19Z-docosapentaenoic acid,
    Synonym 16(17)-epoxy Docosapentaenoic acid
    Abbreviation 16(17)-EpDPE
6. Formal name: (±) 19(20)-epoxy-4Z,7Z,10Z,13Z,16Z-docosapentaenoic acid,
    Synonym 19(20)-epoxy Docosapentaenoic acid
    Abbreviation 19(20)-EpDPE Any of these epoxides, or combinations of any of these, can be administered in the compositions and methods.

5. Formulation and Administration

In various embodiments of the compositions, the agent that increases epoxygenated fatty acids (e.g., an inhibitor of sEH, an EET, an epoxygenated fatty acid, and mixtures thereof) is co-administered with the population of stem cells.

In some embodiments, the agent that increases epoxygenated fatty acids comprises an epoxide of EPA, an epoxide of DHA, or epoxides of both, and an sEHI.

The agent that increases epoxygenated fatty acids can be prepared and administered in a wide variety of oral, parenteral and topical dosage forms. In varying embodiments, the agent that increases epoxygenated fatty acids can be administered orally, by injection, that is, intravenously, intramuscularly, intracutaneously, subcutaneously, intraduodenally, or intraperitoneally. The agent that increases epoxygenated fatty acids can also be administered by inhalation, for example, intranasally. Additionally, the agent that increases epoxygenated fatty acids can be administered transdermally. Accordingly, in some embodiments, the methods contemplate administration of compositions comprising a pharmaceutically acceptable carrier or excipient, an agent that increases epoxygenated fatty acids (e.g., an sEHI or a pharmaceutically acceptable salt of the inhibitor and, optionally, one or more EETs or epoxides of EPA or of DHA, or of both), and optionally an anti-inflammatory agent. In some embodiments, the methods comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or *eucalyptus* oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

The agent that increases epoxygenated fatty acids (e.g., an inhibitor of sEH, an EET, an epoxygenated fatty acid, and mixtures thereof), optionally mixed with an anti-inflammatory and/or analgesic agent, can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, sEHI can be mixed into a commercially available cream, Vanicream® (Pharmaceutical Specialties, Inc., Rochester, Minn.) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents that inhibit sEH are topically administered (that is, whether by solid, liquid, lotion, gel, spray, etc.), in various embodiments they are administered at a dosage of about 0.01 mg to 10 mg per 10 $cm^2$. An exemplary dose for systemic administration of an inhibitor of sEH is from about 0.001 µg/kg to about 100 mg/kg body weight of the mammal. In various embodiments, dose and frequency of administration of an sEH inhibitor are selected to produce plasma concentrations within the range of 2.5 µM and 30 nM.

The agent that increases epoxygenated fatty acids (e.g., an inhibitor of sEH, an EET, an epoxygenated fatty acid, and mixtures thereof), optionally mixed with an anti-inflammatory and/or analgesic agent, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification.

A therapeutically effective amount or a sub-therapeutic amount of the agent that increases epoxygenated fatty acids can be co-administered with a population of stem cells. The dosage of the specific compounds depends on many factors that are well known to those skilled in the art. They include for example, the route of administration and the potency of the particular compound. An exemplary dose is from about 0.001 µg/kg to about 100 mg/kg body weight of the mammal. Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics*, 12th Edition, 2010, McGraw-Hill Professional; in a Physicians' Desk Reference (PDR), 68$^{th}$ Edition, 2014, PDR Network; in *Remington: The Science and Practice of Pharmacy*, 21$^{st}$ Ed., 2005, supra; and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, each of which are hereby incorporated herein by reference.

EETs, EpDPEs, or EpETEs are unstable, and can be converted to the corresponding diols, in acidic conditions, such as those in the stomach. To avoid this, EETs, EpDPEs, or EpETEs can be administered intravenously or by injection. EETs, EpDPEs, or EpETEs intended for oral administration can be encapsulated in a coating that protects the compounds during passage through the stomach. For example, the EETs, EpDPEs, or EpETEs can be provided with a so-called "enteric" coating, such as those used for some brands of aspirin, or embedded in a formulation. Such enteric coatings and formulations are well known in the art. In some formulations, the compositions are embedded in a slow-release formulation to facilitate administration of the agents over time.

It is understood that, like all drugs, sEHIs have half-lives defined by the rate at which they are metabolized by or excreted from the body, and that the sEHIs will have a period following administration during which they are present in amounts sufficient to be effective. If EETs, EpDPEs, or EpETEs are administered after the sEHI is administered, therefore, it is desirable that the EETs, EpDPEs, or EpETEs be administered during the period during which the sEHI are present in amounts to be effective in delaying hydrolysis of the EETs, EpDPEs, or EpETEs. Typically, the EETs, EpDPEs, or EpETEs are administered within 48 hours of administering an sEH inhibitor. Preferably, the EETs, EpDPEs, or EpETEs are administered within 24 hours of the sEHI, and even more preferably within 12 hours. In increasing order of desirability, the EETs, EpDPEs, or EpETEs are administered within 10, 8, 6, 4, 2, hours, 1 hour, or one half hour after administration of the inhibitor. When co-administered, the EETs, EpDPEs, or EpETEs are preferably administered concurrently with the sEHI.

6. Methods of Monitoring

Clinical efficacy can be monitored using any method known in the art. Measurable parameters to monitor efficacy will depend on the condition being treated. For monitoring the status or improvement of one or more symptoms associated with cardiomyopathy, measurable parameters can include without limitation, auditory inspection (e.g., using a stethoscope), blood pressure, electrocardiogram (EKG), magnetic resonance imaging (MRI), changes in blood markers, and behavioral changes in the subject (e.g., appetite, the ability to eat solid foods, grooming, sociability, energy levels, increased activity levels, weight gain, exhibition of increased comfort). These parameters can be measured using any methods known in the art. In varying embodiments, the different parameters can be assigned a score. Further, the scores of two or more parameters can be combined to provide an index for the subject.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, in the case of cardiomyopathy, observation of the improvement of cardiac function (e.g., blood pressure in appropriate range, stable heart rhythm or reduction or absence of arrhythmias, changes in blood markers, and/or behavioral changes in the subject (e.g., increased appetite, the ability to eat solid foods, improved/increased grooming, improved/increased sociability, increased energy levels, improved/increased activity levels, weight gain and/or stabilization, exhibition of increased comfort) after one or more co-administrations of stem cells with an agent indicates that the treatment or prevention regime is efficacious. Likewise, observation of reduction or decline of cardiac function (e.g., blood pressure in appropriate range, unstable heart rhythm or continued presence or increased arrhythmias, changes in blood markers, and/or behavioral changes in the subject (e.g., decreased appetite, the inability to eat solid foods, decreased grooming, decreased sociability, decreased energy levels, decreased activity levels, weight loss, exhibition of increased discomfort) after one or more co-administrations of stem cells with an agent indicates that the treatment or prevention regime is not efficacious.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have the disease condition subject to treatment (e.g., cardiomyopathy), nor are at risk of developing the disease condition subject to treatment (e.g., cardiomyopathy). In such cases, if the value of the measurable biomarker or clinical parameter approaches the control value, then treatment is considered efficacious. In other embodiments, the individuals in the control population have not received prior treatment and have been diagnosed with the disease condition subject to treatment (e.g., cardiomyopathy). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

7. Kits

Further provided are kits, stents and patches comprising a population of stem cells and one or more agents that increase the production or levels of EETs. Embodiments of the stem cells and one or more agents that increase the production or levels of EETs are as described above and herein. In some embodiments, the stem cells are provided in an appropriate container, e.g., a vial, a tube, a pouch, a bag. Stem cell coated or loaded stents are known in the art and find use, e.g., in the methods and kits, e.g., as described in Raina, et al., *Heart.* 2014 June; 100(Suppl 3):A88-A89; Savchenko, et al., *Vestn Rentgenol Radiol.* 2013 July-August; (4):41-6; Wang, et al., *Cardiovasc Res.* 2009 Dec. 1; 84(3):461-9; Motwani, et al., *Biotechnol Appl Biochem.* 2011 January-February; 58(1):2-13; Wu, et al., *J Biomed Mater Res A.* 2011 Sep. 1; 98(3):442-9; and Intl. Patent Publ. No. WO 2008/094936. Patches, including cardiac patches, which can serve as repositories for the delivery of stem cells are also known in the art and find use, e.g., in the methods and kits, e.g., as described in Kim, et al., Integr Biol (Camb). 2012 September; 4(9): 1019-33; LeBlanc, et al., *Stem Cells Transl Med.* 2013 November; 2(11):896-905; Lam, et al., *Tissue Eng Part A.* 2013 March; 19(5-6):738-47; Wang, et al., Antioxid Redox Signal. 2014 Apr. 30; Wickham, et al, *J Biomed Mater Res B Appl Biomater.* 2014 Mar. 24; and Martinez-Ramos, et al., *Tissue Eng Part C Methods.* 2014 Mar. 14.

EXAMPLES

The following examples are offered to illustrate, but not to limit the claimed invention.

Example 1

Beneficial Effects of sEHIs on Cardiac Remodeling Post MI

Figure 2:
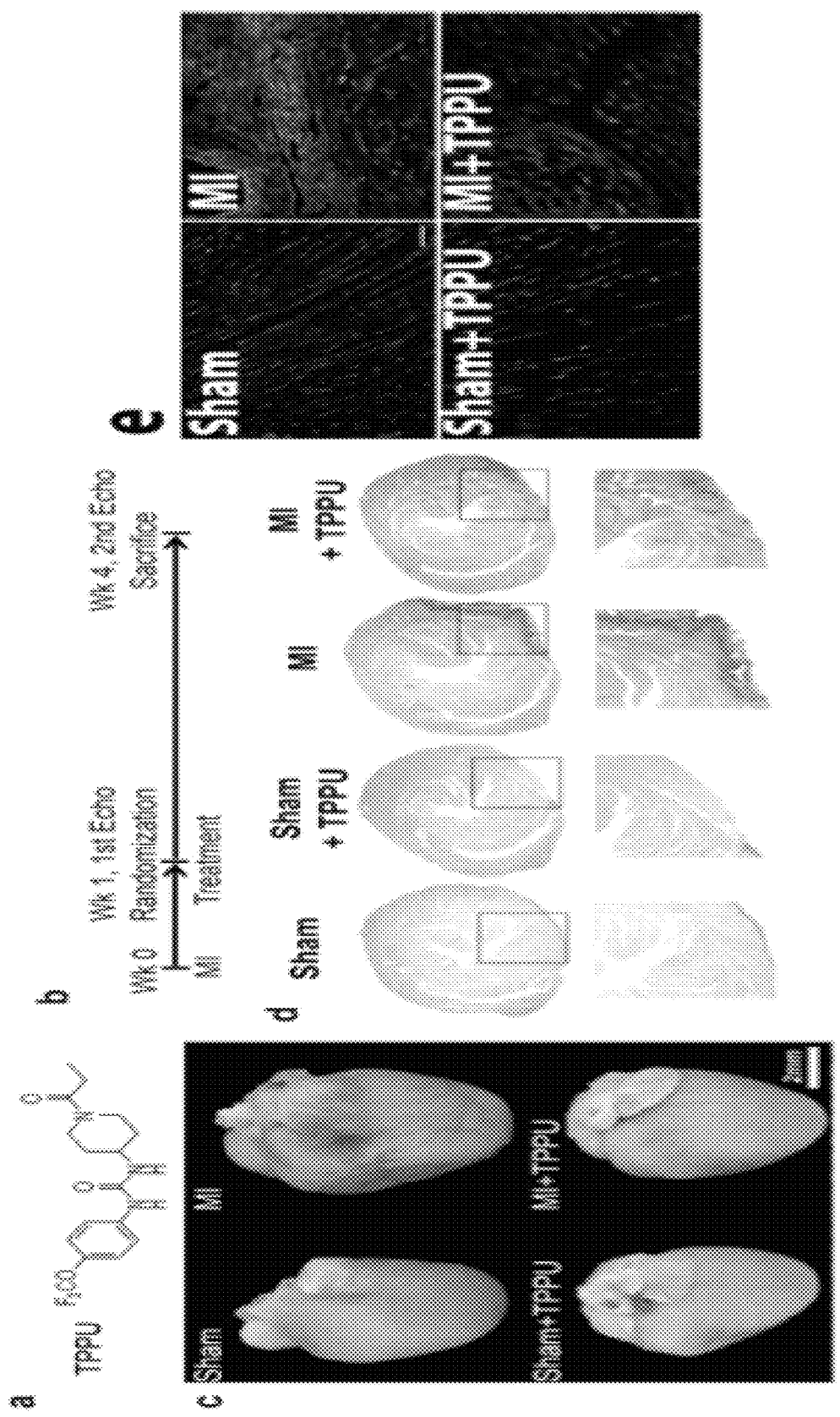
FIGS. 2A-E illustrate beneficial effects of TPPU in ventricular remodeling post MI. a, Structure of the sEHI (TPPU). b, Experimental protocol. c, Examples of whole hearts from MI & sham mice with & without TPPU. d, The amount of collagen deposition in cardiac sections (Sirius red). e, Confocal images of wheat germ agglutinin showing a significant decrease in collagen deposition in MI mice with TPPU vs. MI alone (scale bar, 50 mm). n=3 per group.
Figure 3:
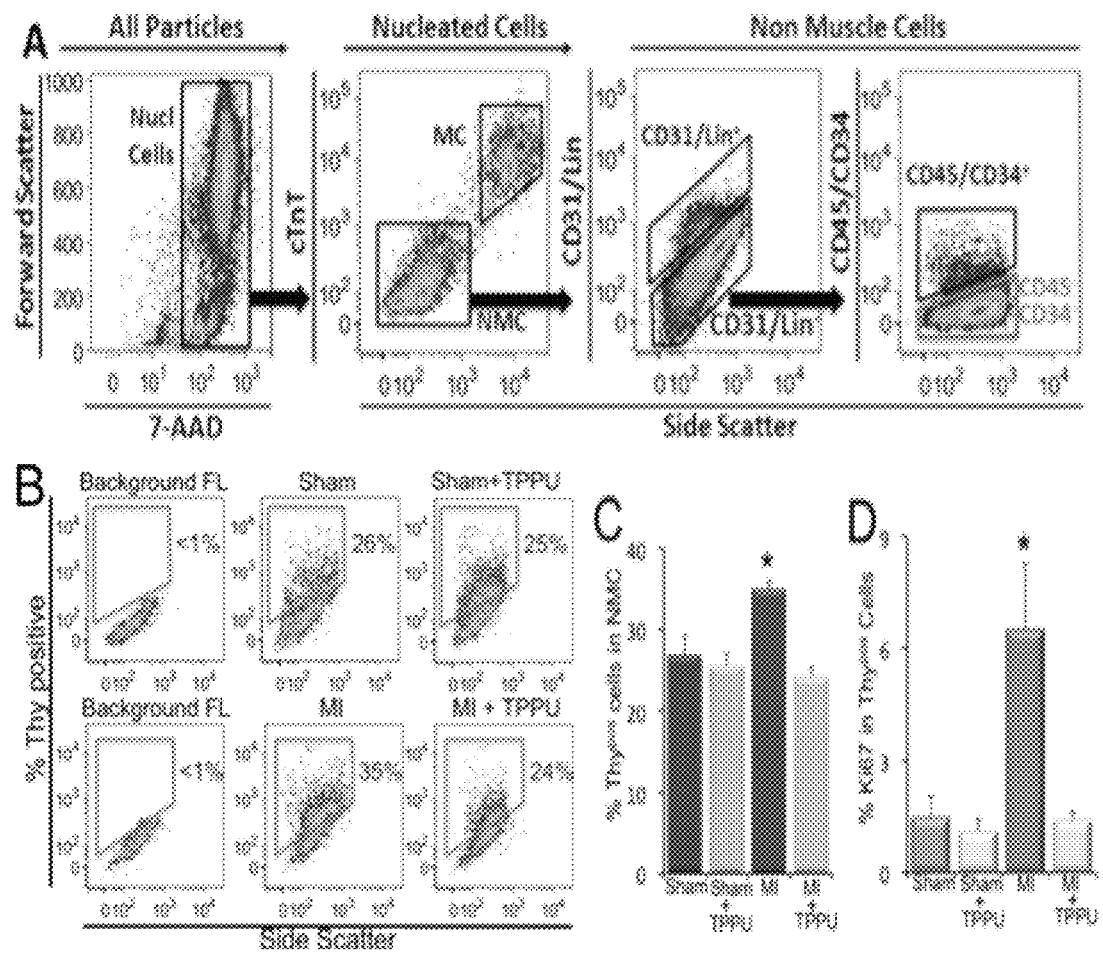
FIGS. 3A-D illustrate flow cytometric analysis of Thy1.2+ cells from cardiac tissue. A) The selection of nucleated cells (Nucl cells) based on the incorporation of 7AAD, the separation of myocytes (MCs) from non-muscle cells (NMC) and the separation of Thy1.2+ cells. B) Thy1.2+ cells from the four groups of animals. C, D) Percentages of Thy1.2+ cells and Ki67 positivity in Thy1.2+ cells respectively *P<0.05. n=3 per group. Error bars=standard error.

We have demonstrated the beneficial effects of several sEHIs in cardiac remodeling in clinically relevant models of cardiac hypertrophy, fibrosis and failure (1-8). A sEHI, TPPU (1-trifluoromethoxy phenyl-3-(1-propionylpiperidine-4-yl) urea, FIG. 2a) was started 1 week post MI (FIG. 2b). Treatment with TPPU resulted in a significant reduction in cardiac dilatation and the amount of collagen deposition compared to MI alone (FIG. 2c, d and e). A single-cell based assay using flow cytometry was used to label myocytes (MC) with cardiac-specific troponin T antibody (FIG. 3A). Cardiac fibroblasts were identified as Thy1.2+ and lin−/CD31/CD45/CD34− cells (FIGS. 3A and B) (23). The findings demonstrated a significant increase in Thy1.2+ cells in the remote area from the infarct zone in MI mice compared to sham animals. Treatment with TPPU resulted in a significant decrease in Thy1.2+ fibroblasts (FIG. 3C) and a significant decrease in proliferative fibroblasts (Ki67+) (FIG. 3D) compared to MI alone.

Example 2

Mechanisms Underlying the Observed Beneficial Effects of sEHIs in the Heart

Figure 4:
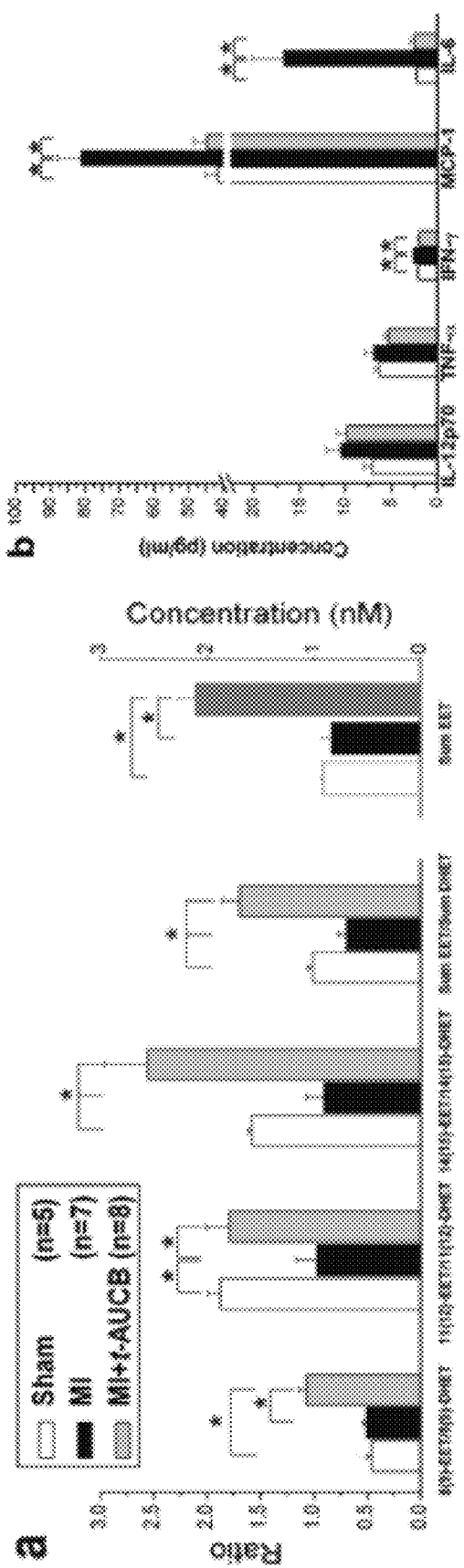
FIGS. 4A-B illustrate plasma levels of selected oxylipin, chemokines and cytokines. A, oxylipin profiling from sham (white bars), MI (black bars) and MI treated with sEHI (t-AUCB) (gray bars) at 3 weeks of follow up. B, serum concentrations of IL-12p70, TNF-α, IFN-γ, MCP-1, and IL-6 of sham (white bars), MI (black bars) and MI treated with sEHI (t-AUCB) (gray bars) at 3 weeks of follow up (*p<0.05).

Our studies provide new insights into the mechanisms of action of sEHIs in cardiac hypertrophy and failure: 1) Using metabolomic profiling, we demonstrate a significant decrease in the EETs/DHETs ratio after thoracic aortic banding and MI, suggesting a heightened inflammatory state; 2) Treatment with sEHIs results in the normalization of the EETs/DHETs ratio and a concomitant reduction in inflammatory cytokines and chemokines (FIG. 4a & b)(5); 3) A significant reduction in myocyte hypertrophy and apoptosis (5) and finally; 4) Inhibition of the activation of NF-κB pathway in cardiac myocytes (1)

Research Design and Methods:

This example tests the survival, engraftment, integration, and function of transplanted hiPSC-CMs in the acute model of MI with and without sEHIs treatment.

Tissue injury from MI results in robust inflammatory responses, involving the synthesis and release of chemo- and cytokines and the recruitment of fibroblasts, which may form physical barriers at the site of injury and inhibit stem cell integration and survival. Our recent results have demonstrated that sEHIs reduce pro-inflammatory cytokines and chemokines (IL-6, IFN-γ, TNF-α and MCP-1, FIG. 4) and are anti-fibrotic, capable of reducing collagen deposition in the injured myocardium (8). Therefore, treatment with sEHIs in the MI model results in the improvement in the survival and functional integration of hiPSC-CMs in NSG mice. To test, inhibitors of sEH enzyme were administered in a murine myocardial infarction (MI) model. In addition, the role of sEH enzyme was directly tested using gene-targeted sEH null mutant mice (24).

Figure 5:
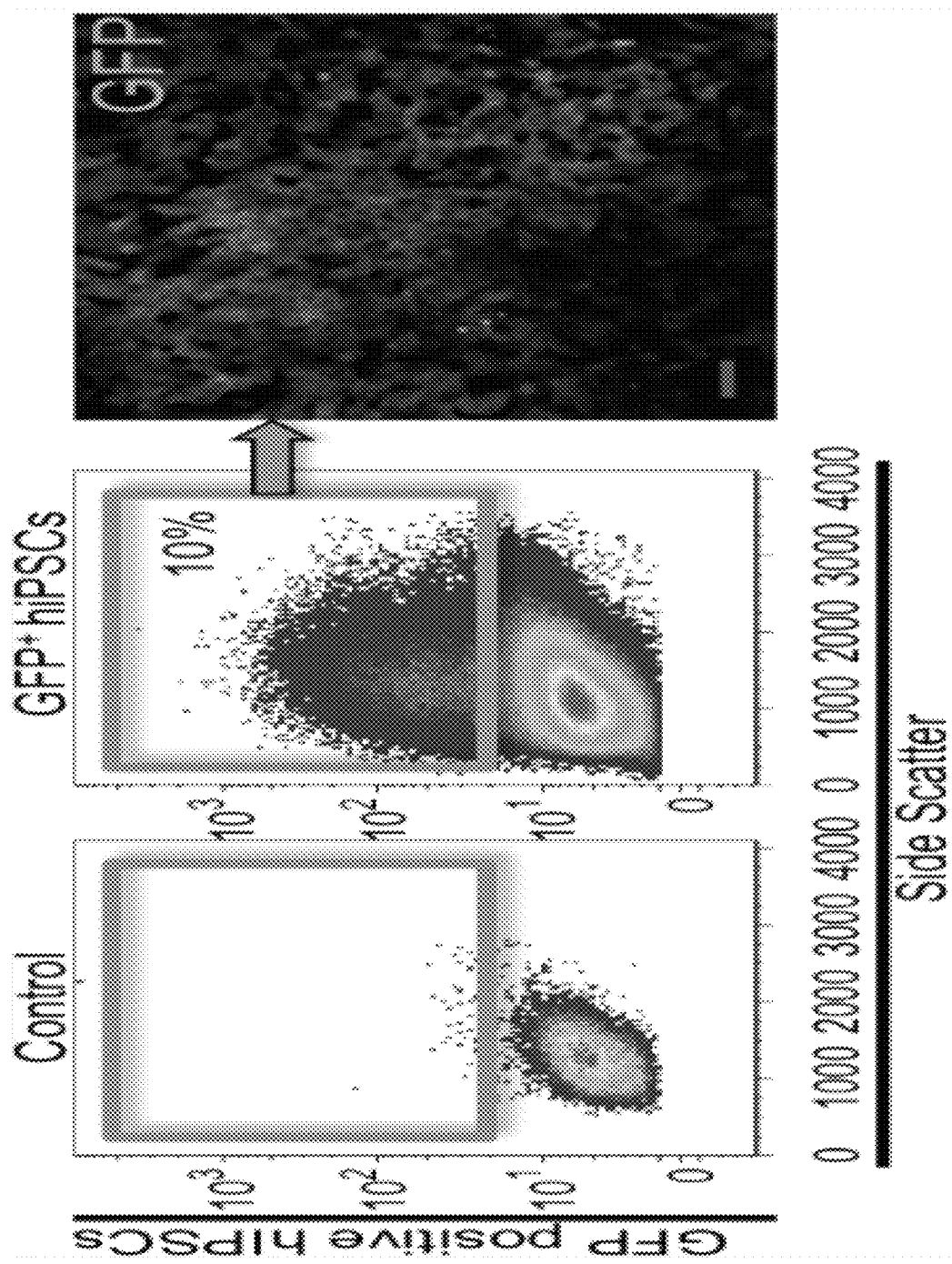
FIG. 5 illustrate FACS of GFP+ hiPSCs and confocal images of cultured GFP+ hiPSCs. Scale bar=50 µM.

Experimental Design: HiPSCs containing the puromycin gene under the α-myosin heavy chain promoter were transduced with a double fusion construct of reporter genes; firefly luciferase for bioluminescence imaging and green fluorescent protein (GFP) (25). GFP+ hiPSCs were sorted using florescent activated cell sorter (FACS) (FIG. 5), differentiated into beating clusters of hiPSC-CMs (26) and enriched with puromycin treatment.

Mouse MI model: MI were generated in 10- to 12-week-old male NSG and sEH null mutant (sEH$^{-/-}$) mice as we have previously described (8). One week after the surgery, NSG mice were randomized into six different groups: 1) Sham±sEHI, 2) MI±sEHI and 3) MI+hiPSC-CM±sEHI. Transplantation of hiPSC-CMs into the border zones (27) was performed using ultrasound (VisualSonics Vevo 2100) guided injection and mice were treated with sEHIs (15 mg/L) in drinking water one week after surgery for a period of 3 weeks. Similarly, a total of 6 groups were required to test the effects of genetic deletion of sEH (Ephx2) including: 1) Sham, 2) MI, 3) MI+hiPSC-CM in Ephx2$^{-/-}$ animals compared to wild-type (WT) littermates. Cardiac fibrosis was evaluated using hydroxyproline assay, histology, flow cytometry, and immunofluorescence confocal imaging as we have previously described (8). All the animals will undergo in vivo experimentation for 3 weeks at the end of which the animals were sacrificed for in vitro analyses.

Figure 6:
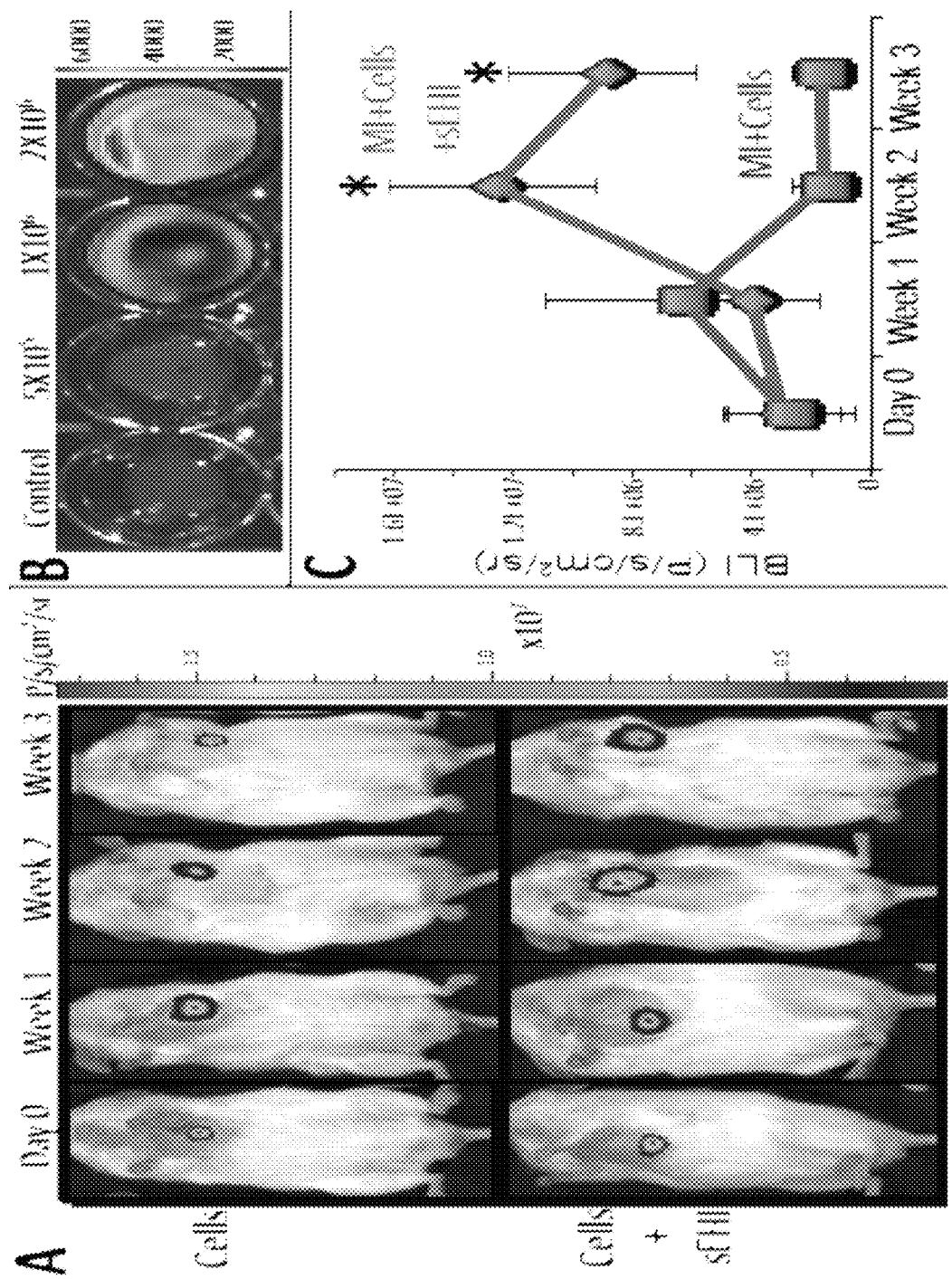
FIGS. 6A-C illustrate in vivo Bioluminescence (BLI) Imaging: A. Longitudinal imaging of transplanted hiPSC-CMs (Cells) in NSG mice with sEHI treatment (bottom panel) and without sEHI treatment (top panel). B. In vitro BLI imaging of varying numbers of GFP+ hiPSCs. C. Quantification of BLI signals showing a significant increase in BLI in sEHI treated mouse (Blue) vs non-treated mouse (red). * P<0.05.

I. In Vivo Analyses:

Longitudinal in vivo bioluminescence imaging (BLI). To quantify the survival and engraftment of transplanted hiPSC-CMs over time, in vivo BLI imaging was performed at the UC Davis Center for Molecular and Genomic Imaging using the IVIS Xenogen system. Our exciting BLI data shows a significant improvement in the survival of GFP+ hiPSC-CMs in NSG mice with MI at week 4 with sEHI treatment vs. no sEHI treatment (FIG. 6A-B). Quantification by flow cytometry showed double the number of GFP+ hiPSC-CMs in the sEHI treated mice (10±0.2%) compared to the untreated mice (5±1%) (FIG. 6C).

Figure 7:
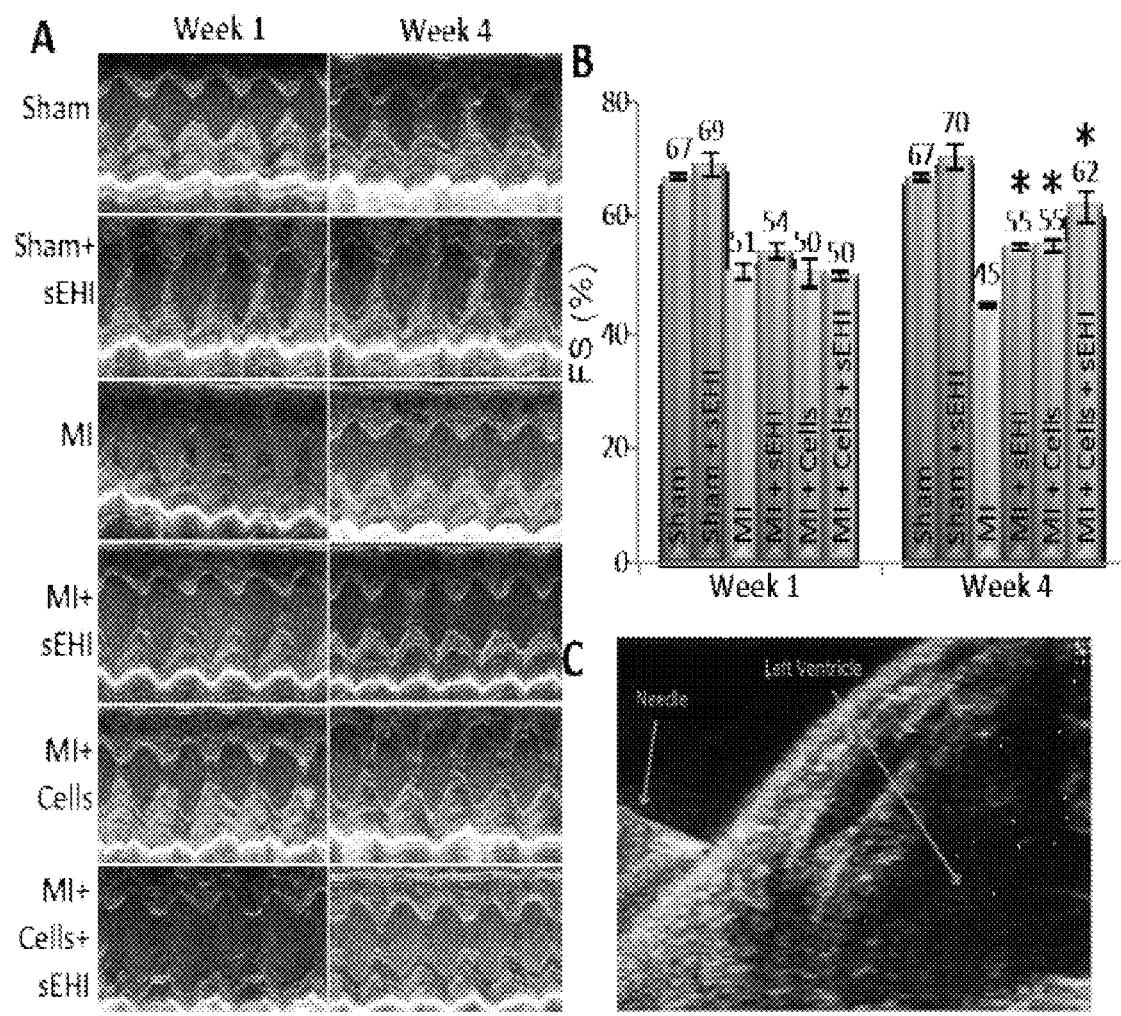
FIGS. 7A-C illustrate transplantation of hiPSCs in NSG mice: A Echocardiogram tracings at 1 and 4 weeks post-operation in the six groups (Sham±sEHI, MI±sEHI, &MI+hiPSC-CM±sEHI) B. Quantification of FS in the six groups. Numbers represents FS %. Cells=hiPSC-CMs C. Ultrasound-guided injection of hiPSC-CMs in the left ventricle of the mouse heart, *P<0.05.

Functional analysis by echocardiography was performed to evaluate the systolic and diastolic function. We have obtained exciting data from six groups of animals (FIG. 7) demonstrating a significant improvement in the fractional shortening (FS) as assessed using motion-mode echocardiography in the MI+hiPSC-CM+sEHI group (62±2.6%) compared to MI+sEHI (55±0.6%), MI+hiPSC-CMs (55±1.1%), and MI alone (45±0.5%) groups at 4 week (FIG. 7, $*P<0.05$, ANOVA). As expected, there was a decrease in the FS in the MI group from one week (51±1.1%) to 4 week (45±0.5%), suggesting adverse remodeling in the MI alone group. Indeed, treatment with sEHI and hiPSC-CMs in the MI animal resulted in an added improvement in the fractional shortening (FS) compared with the MI alone.

Figure 8:
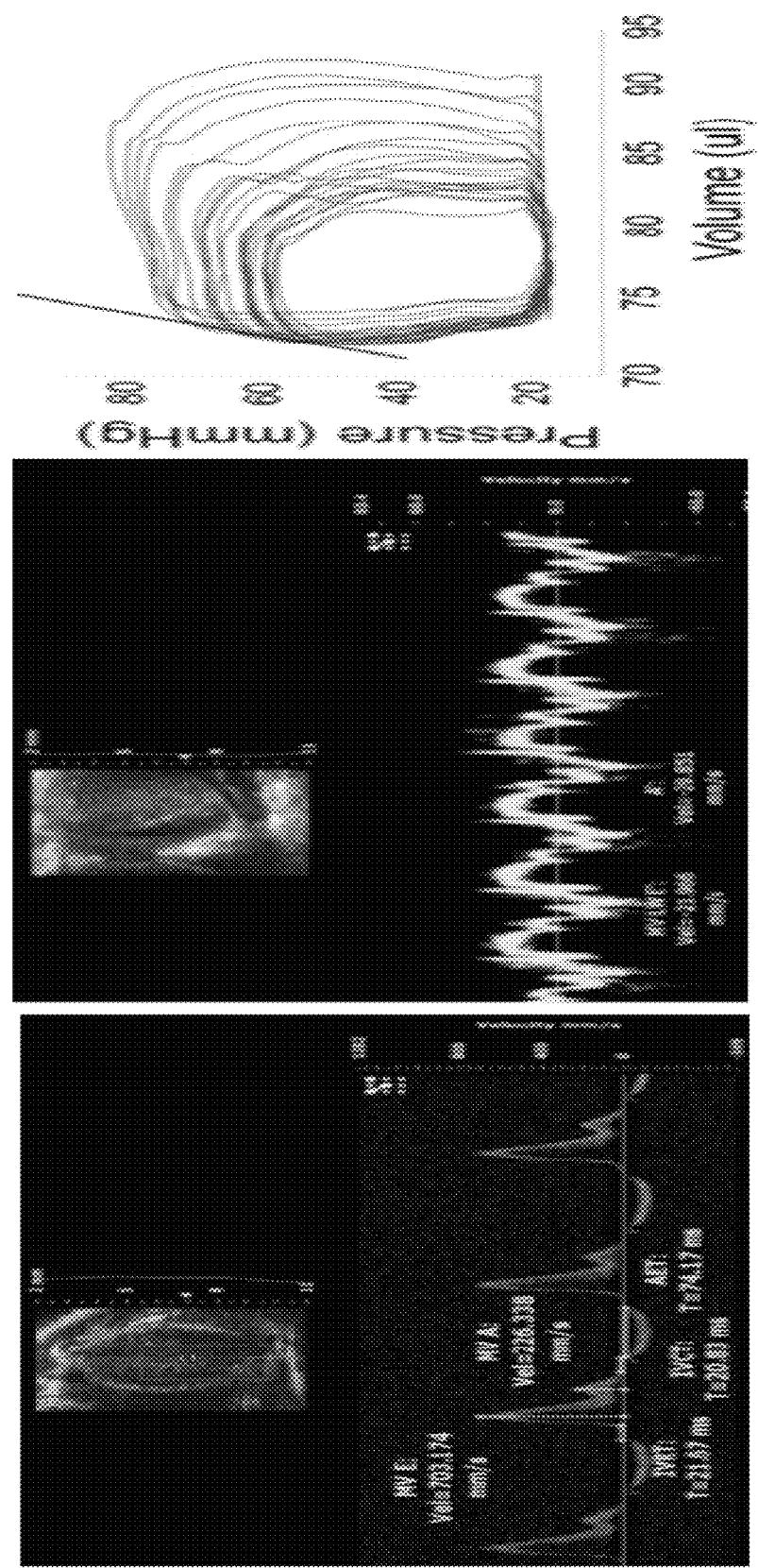
FIG. 8 illustrates assessment of diastolic function and in vivo hemodynamic analyses: Examples of pulsed-wave mitral inflow analyses (Left Panel) and pulsed-wave tissue Doppler imaging (TDI, Middle Panel) in the mouse model. Pulsed-wave TDI was performed at the lateral mitral annulus using apical 4 chamber view. Examples of PV loops (Right Panel) in a sham animal.

In vivo hemodynamic monitoring was performed using a four-electrode PV catheter (Millar Instruments) to record chamber volume by impedance and pressure by micromanometry (28). Different parameters were assessed including LV end diastolic pressure. PV loops were constructed before and during transient reduction of preload to generate specific systolic and diastolic function indexes, LV afterload (indexed by arterial elastance), ejection fraction, contractile function as assessed through load-independent parameters (maximal power index & preload recruitable stroke work), & diastolic function (LV stiffness constant, tau and peak rate of pressure decline ($dP/dt_{min}$) (FIG. 8) (28, 29).

Figure 9:
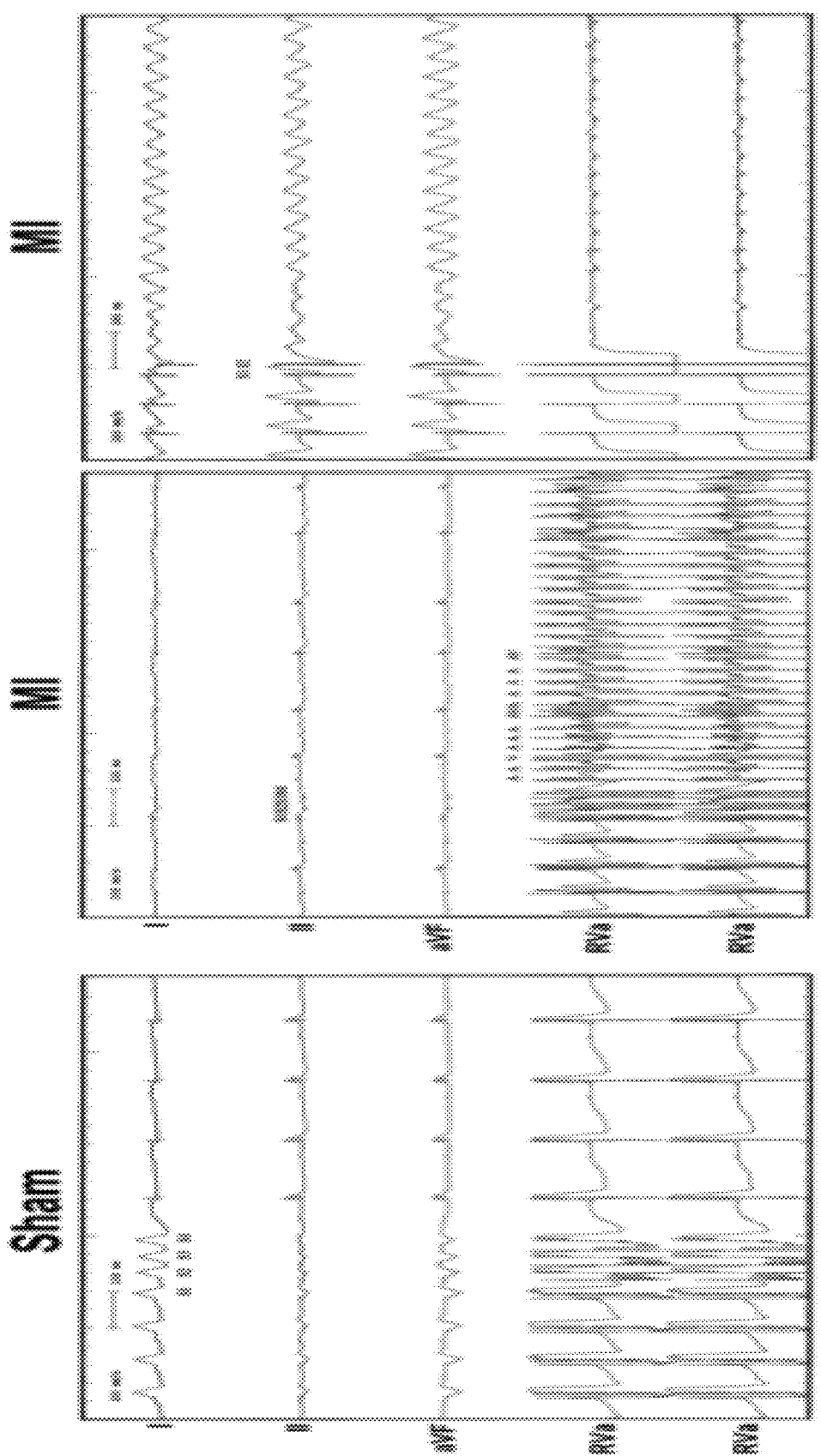
FIG. 9 illustrates in vivo electrophysiologic studies in sham and MI model. Examples of inducible atrial and ventricular arrhythmias in the MI model using program stimulation (Middle and Right Panels).

In vivo electrophysiologic studies (5, 30) were performed to test for inducible cardiac arrhythmias and finally optical imaging was performed to assess conduction velocity and action potential duration (FIG. 9) (31-33). The spectrally distinct GFP was excited to image hiPSC-CMs-derived cells from the epicardial surface to assess the engraftment and integration.

Figure 10A:
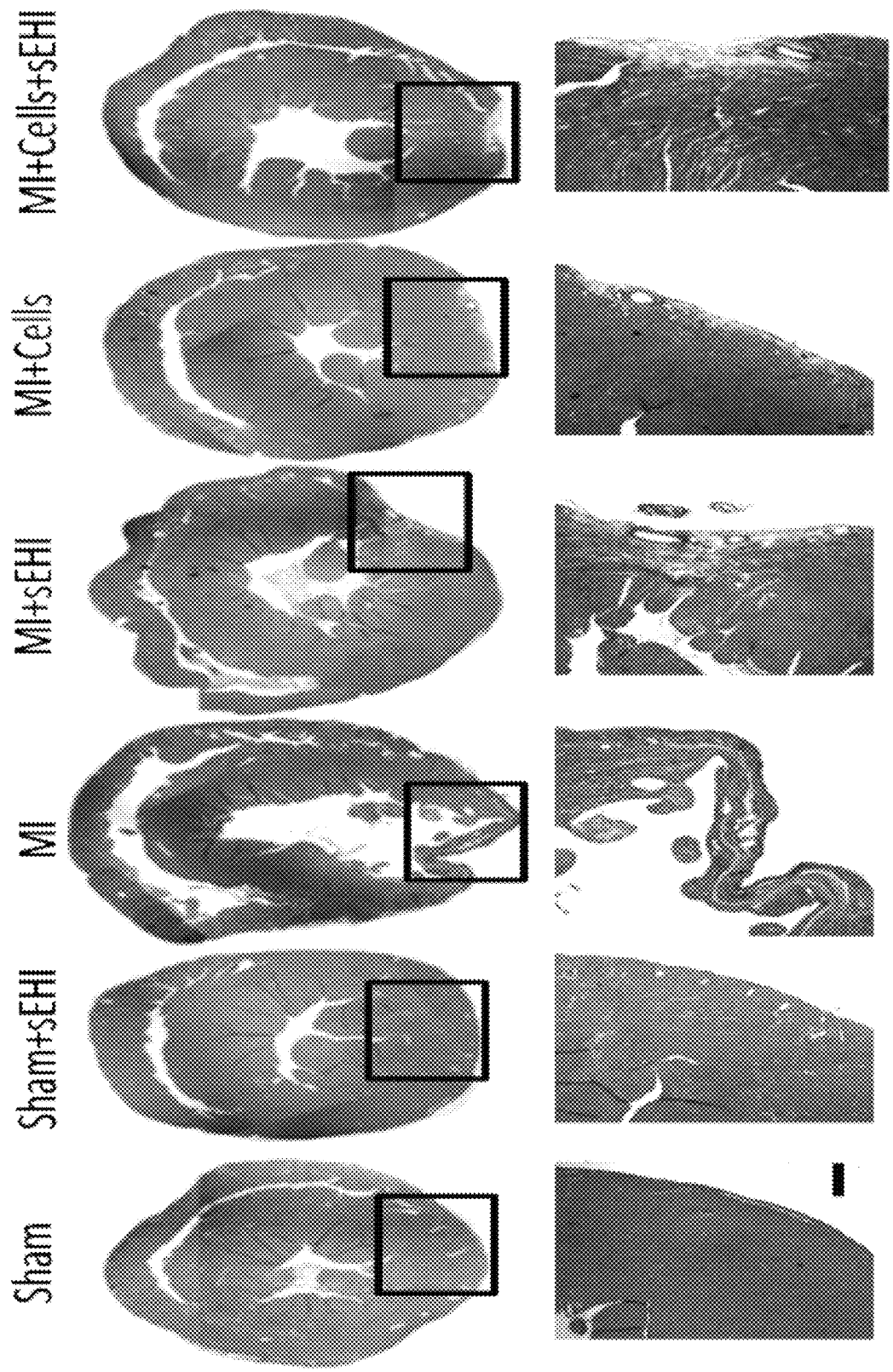
FIGS. 10A-B. A) Cardiac sections stained with Trichrome demonstrating collagen deposition. B) Immunofluorescence images of cardiac sections showing the presence of GFP+ cells. Scale bar=200 µM. Cells=hiPSC-CMs.

II. In Vitro Analyses:

Histology: To quantify cardiac fibrosis, cardiac sections from six groups of animals were examined using Masson's Trichrome stain. Our data with the six groups of animals shows a decrease in fibrosis in the hiPSC-CM+sEHI group compared to the MI alone mice (FIG. 10A).

Figure 10B:
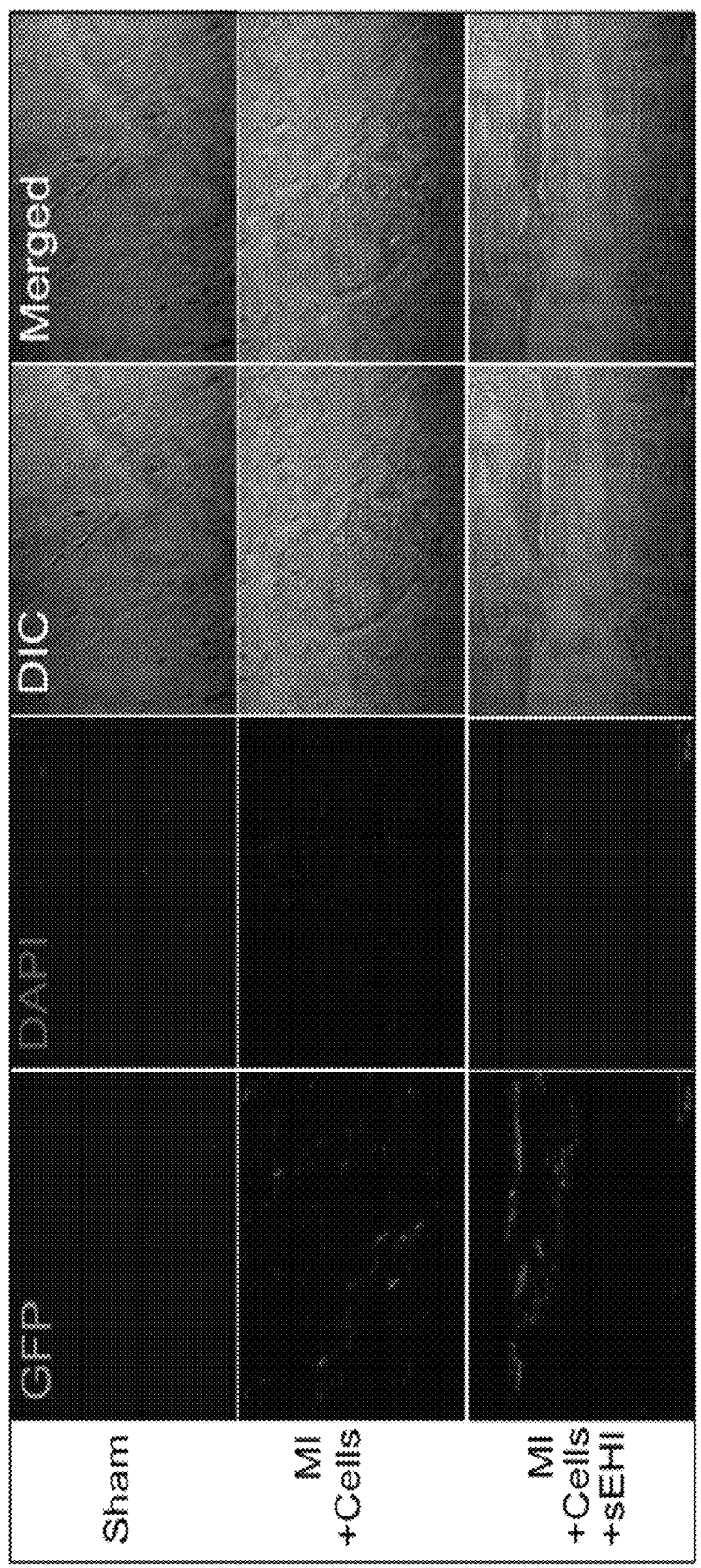

Immunofluorescence Confocal Microscopy: The engraftment and integration of transplanted hiPSC-CMs were assessed using immunofluorescence confocal microscopy and histology to detect donor cells (GFP+) and cardiac-specific cell types as well as the integration between transplanted hiPSC-CMs and host cardiomyocytes using antibodies specific for connexin. Our data shows an increased presence of GFP+ cells in the MI+sEHI mice compared to MI alone (FIG. 10B).

Single-cell based assays using flow cytometry were performed as described previously (34) to quantify the number and proliferative capacity of GFP+ hiPSC-CMs using troponin T (cTnT) antibodies and different populations of cardiac fibroblasts using various markers (Thy1.2, FSP-1, DDR2) (23, 35-39). The hiPSC-CM volume were analyzed using Coulter Multisizer 4 as previously described (40).

Metabolic profiling of oxylipin levels were performed using LC-MS/MS as we have described (1-7). The increase in the EETs/DHETs ratios will directly document the target engagement by sEHIs.

Second harmonic generation (SHG) microscopy, a novel imaging technique were used to image and quantify the myofilament, structures, and dynamics to assess the contractility and maturation of hiPSC-CM non-invasively (FIG. 11). SHG microscopy is a non-linear label-free technique that can directly image the stem cell derived sarcomeres based on the unique intrinsic property of the myosin rod domains to generate a signal at twice the frequency and half the wavelength of the laser beam used to excite the sarcomeres.

Example 3

Directly Testing the Molecular Mechanisms Underlying the Beneficial Effects of sEHIs on Stem Cell Survival and Integration Oxidative stress activates Erk1/2 and NF-κB, which further causes apoptosis and reducing the oxidative stress shows an increased stem cell engraftment (Song, et al., *Stem Cells.* 2010; 28:555-563; Tusi, et al., *Biomaterials.* 2011; 32:5438-5458; Ahmad, et al., Toxicology Letters. 2012; 208:149-161). The nuclear translocation of NF-κB is required for apoptosis as well (Tusi, et al., *Biomaterials.* 2011; 32:5438-5458; Ahmad, et al., Toxicology Letters. 2012; 208:149-161). EETs have been shown to reduce oxidative stress and apoptosis in other organs (Chen, et al., Cell Physiol Biochem. 2014; 33(6): 1663-80; Li, et al., *Mol Pharmacol.* 2013 December; 84(6):925-34). Here, we determined whether treatment with sEHIs reduces oxidative stress and apoptosis in the host myocardial cells as well as the engrafted hiPSC-CMs by inactivating Erk1/2 and NF-κB. To test, we directly examine the oxidative stress (production of ROS) and apoptosis in the cardiomyocytes (CMs), non-myocyte cells (NMCs) and transplanted hiPSC-CMs in the sEHI treated and non-treated groups.

In addition, the mechanistic basis for the observed beneficial effects was tested in the transplanted hiPSC-CMs. EETs regulate gene expression by maintaining NF-κB in an inactive state (1, 19). Since sEH enzyme converts EETs to inactive DHET, increased levels of EETs by treatment with sEHIs prevent the activation and nuclear localization of NF-κB in the transplanted hiPSC-CMs.

Experimental Design: Two sEHIs with significantly different chemical structures (TPPU containing the piperidine ring and t-AUCB containing the adamantane ring) were used (Table 2, supra).

Apoptosis Assay: The degree of apoptosis was analyzed using single-cell based flow cytometry in the NMCs, cardiomyocytes (CM) and transplanted GFP+ hiPSC-CMs in sEHI treated and non-treated mice as described previously (34) using propidium iodide and Annexin V (Life Technologies). Our apoptosis assay data in all cardiac cells indicates that there was a significant decrease in apoptosis in NMCs and CMs fractions in the MI+hiPSC-CMs+sEHI group compared to the MI, MI+hiPSC-CMs, MI+sEHI groups (FIG. 12). Our exciting analysis in the transplanted GFP+ hiPSC-CMs shows a significant decrease in apoptotic cells in the MI+hiPSC-CMs+sEHI group compared to MI+hiPSC-CMs without sEHI treatment (FIG. 13).

Oxidative Stress Assay: The oxidative stress in the myocardium was analyzed using isolated single cells for the production of ROS using flow cytometry. The cell-permeant CellRox (Life technologies) probe remains non-fluorescent while in a reduced state and exhibits bright fluorescence upon oxidation by ROS. Our assay data in all cardiac cells indicates that there was a significant decrease in the ROS production in NMCs and CM fractions in the MI+hiPSC-CMs+sEHI group compared to the MI, MI+hiPSC-CMs, MI+sEHI groups (FIG. 14). In addition, we have obtained additional data in the transplanted GFP+ hiPSC-CMs which demonstrate a significant decrease in ROS production in the MI+hiPSC-CMs+sEHI group compared to MI+hiPSC-CMs without sEHI treatment (FIG. 15).

Figure 16A:
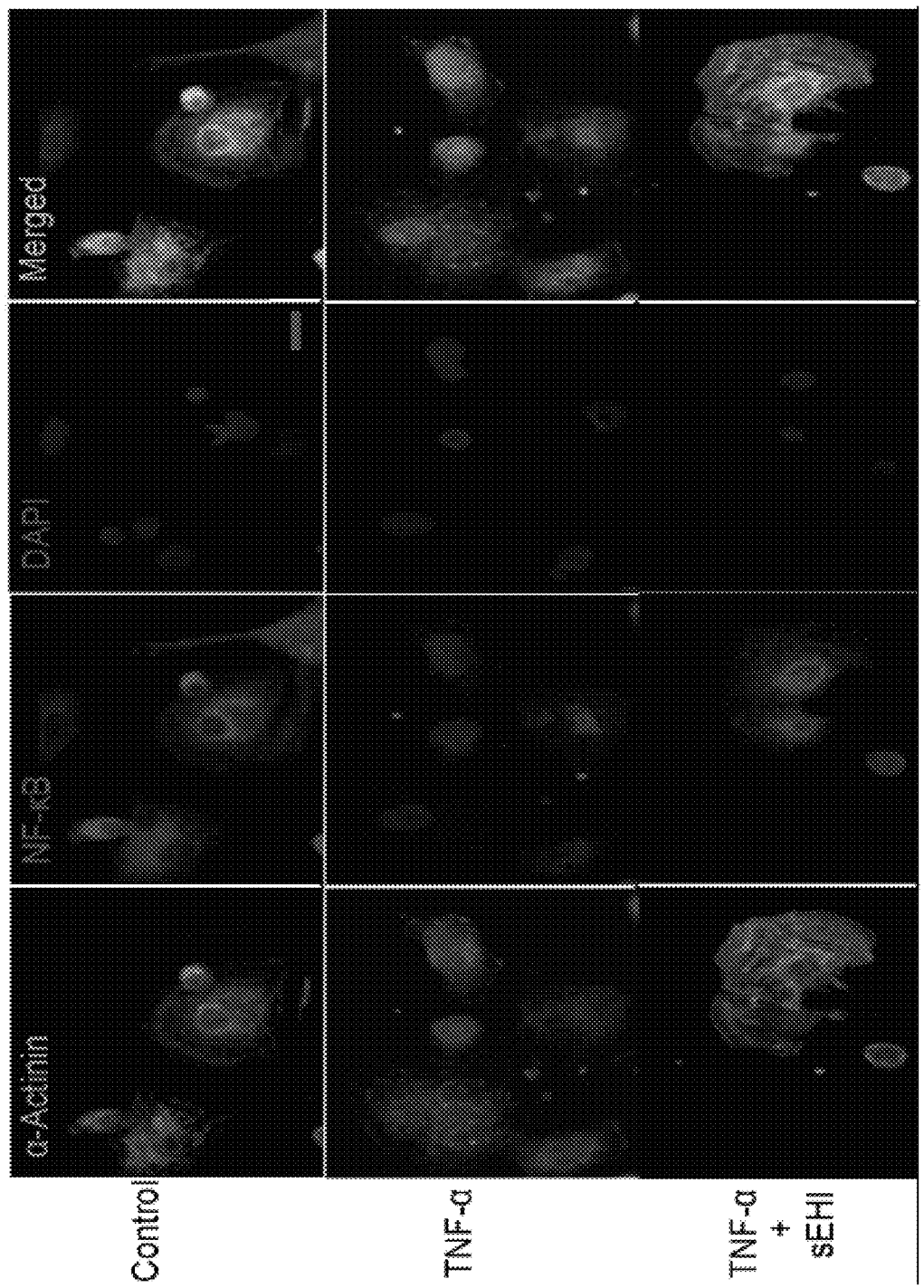

Activation of NF-κB: NF-κB represents one of the critical players in the cytokine-mediated inflammation. NF-κB was maintained in the inactive form when bound to IκB, which was degraded by IκB kinase. Degradation of IκB releases the NF-κB dimer from the cytosol leading to nuclear translocation of NF-κB and gene activation. Since sEHIs prevent the conversion of EETs and EETs in turn inhibit IκB kinase (19), treatment with sEHI may prevent the activation and nuclear translocation of NF-κB in the transplanted stem cells exposed to inflammatory cytokines. Indeed, we have obtained exciting data that demonstrate an increased nuclear translocation of NF-κB in the cultured hiPSC-CMs upon TNF-α stimulation (20 ng/ml for 20 min). This effect was inhibited by the treatment of sEHI (FIG. 16). We will further test the activation of NF-κB in the in vivo models of MI using confocal microscopy and western blotting as previously described (1). We also tested whether sEHIs can block the activation of NF-κB using Western blot analysis (FIG. 16B). Total IκB and phosphorylated-IκB (pIκB) levels assessed after TNF-α stimulation showed a decrease in IκB level and an increase in the pIκB levels associated with the activation of NF-κB. TNF-α stimulation showed an increase in the level of NF-κB in the nuclear fraction, which was not seen in sEHI treated cells (FIGS. 16C and 16D).

Statistical analyses: All data were tested for normality by the Shapiro-Wilk test and homogeneity of variances were assessed using the Levene's test (42). Repeated measures of analysis of variance (RM-ANOVA) combined with post hoc analyses were performed with treatment as a between-group variable.

Treatment with sEHIs results in an increase in the survival, engraftment, and integration of transplanted hiPSC-CMs with an increase in the formation of gap junctions between transplanted hiPSC-CMs and host cardiac myocytes compared to the treatment with hiPSC-CMs alone. There was a concomitant decrease in fibrosis associated with an improvement in cardiac function and a decrease in inducible arrhythmias. At the in vivo level, this translates into an improvement in cardiac function associated with a reduction in arrhythmia inducibility. There may be immune rejection of the transplanted stem cells in the sEH null mutant mice. This can be decreased with the use of immunosuppression in the hiPSC-CMs treated sEH null mutant mice. Mechanistically, treatment with sEHIs results in a decrease in cellular apoptosis, as well as a decrease in ROS production and NF-κB activation in transplanted hiPSC-CMs.

REFERENCES

1. Xu D, Li N, He Y, Timofeyev V, Lu L, Tsai H J, Kim I H, Tutej a D, Mateo R K, Singapuri A, Davis B B, Low R, Hammock B D, Chiamvimonvat N. Prevention and reversal of cardiac hypertrophy by soluble epoxide hydrolase inhibitors. Proc Natl Acad Sci USA. 2006; 103: 18733-18738
2. Chiamvimonvat N, Ho C M, Tsai H J, Hammock B D. The soluble epoxide hydrolase as a pharmaceutical target for hypertension. J Cardiovasc Pharmacol. 2007; 50:225-237
3. Ai D, Pang W, Li N, Xu M, Jones P D, Yang J, Zhang Y, Chiamvimonvat N, Shyy J Y, Hammock B D, Zhu Y. Soluble epoxide hydrolase plays an essential role in angiotensin ii-induced cardiac hypertrophy. Proc Natl Acad Sci USA. 2009; 106:564-569
4. Harris T R, Li N, Chiamvimonvat N, Hammock B D. The potential of soluble epoxide hydrolase inhibition in the treatment of cardiac hypertrophy. Congest Heart Fail. 2008; 14:219-224
5. Li N, Liu J Y, Timofeyev V, Qiu H, Hwang S H, Tuteja D, Lu L, Yang J, Mochida H, Low R, Hammock B D, Chiamvimonvat N. Beneficial effects of soluble epoxide hydrolase inhibitors in myocardial infarction model: Insight gained using metabolomic approaches. J Mol Cell Cardiol. 2009; 47:835-845
6. Li N, Liu J Y, Qiu H, Harris T R, Sirish P, Hammock B D, Chiamvimonvat N. Use of metabolomic profiling in the study of arachidonic acid metabolism in cardiovascular disease. Congest Heart Fail. 2011; 17:42-46
7. Qiu H, Li N, Liu J Y, Harris T R, Hammock B D, Chiamvimonvat N. Soluble epoxide hydrolase inhibitors and heart failure. Cardiovasc Ther. 2011
8. Sirish P, Li N, Liu J Y, Lee K S, Hwang S H, Qiu H, Zhao C, Ma S M, Lopez J E, Hammock B D, Chiamvimonvat N. Unique mechanistic insights into the beneficial effects of soluble epoxide hydrolase inhibitors in the prevention of cardiac fibrosis. Proc Natl Acad Sci USA. 2013; 110:5618-5623
9. Levy D, Garrison R J, Savage D D, Kannel W B, Castelli W P. Prognostic implications of echocardiographically determined left ventricular mass in the framingham heart study. N Engl J Med. 1990; 322:1561-1566
10. Ho K K, Pinsky J L, Kannel W B, Levy D. The epidemiology of heart failure: The framingham study. J Am Coll Cardiol. 1993; 22:6A-13A
11. Dominguez L J, Parrinello G, Amato P, Licata G. Trends of congestive heart failure epidemiology: Contrast with clinical trial results. Cardiologia. 1999; 44:801-808
12. Cohn J, Archibald D, Ziesche S, Franciosa J, Harston W, Tristani F, Dunkman W, Jacobs W, Francis G, Flohr K, Goldman S, Cobb F, Shah P, Saunders R, Fletcher R, Loeb H, Hughes V, Baker B. Effect of vasodilator therapy on mortality in chronic congestive heart failure: Results of a veterans administration cooperative study. N Engl J Med. 1986; 314:1547-1552
13. Dimmeler S, Burchfield J, Zeiher A M. Cell-based therapy of myocardial infarction. Arteriosclerosis, thrombosis, and vascular biology. 2008; 28:208-216
14. Dimmeler S, Zeiher A M. Cell therapy of acute myocardial infarction: Open questions. Cardiology. 2009; 113:155-160
15. Dimmeler S, Losordo D. Stem cells review series: An introduction. Circ Res. 2011; 109:907-909
16. Laflamme M A, Chen K Y, Naumova A V, Muskheli V, Fugate J A, Dupras S K, Reinecke H, Xu C, Hassanipour M, Police S, O'Sullivan C, Collins L, Chen Y, Minami E, Gill E A, Ueno S, Yuan C, Gold J, Murry C E. Cardiomyocytes derived from human embryonic stem cells in pro-survival factors enhance function of infarcted rat hearts. Nature biotechnology. 2007; 25:1015-1024
17. Chen I Y, Wu J C. Cardiovascular molecular imaging: Focus on clinical translation. Circulation. 2011; 123:425-443

18. Zhang W Y, Ebert A D, Narula J, Wu J C. Imaging cardiac stem cell therapy: Translations to human clinical studies. Journal of cardiovascular translational research. 2011; 4:514-522
19. Spector A A, Fang X, Snyder G D, Weintraub N L. Epoxyeicosatrienoic acids (eets): Metabolism and biochemical function. Progress in lipid research. 2004; 43:55-90
20. Zeldin D C, Moomaw C R, Jesse N, Tomer K B, Beetham J, Hammock B D, Wu S. Biochemical characterization of the human liver cytochrome p450 arachidonic acid epoxygenase pathway. Arch Biochem Biophys. 1996; 330:87-96
21. Imig J D. Epoxides and soluble epoxide hydrolase in cardiovascular physiology. Physiol Rev. 2012; 92:101-130
22. Morisseau C, Hammock B D. Epoxide hydrolases: Mechanisms, inhibitor designs, and biological roles. Annu Rev Pharmacol Toxicol. 2005; 45:311-333
23. Hudon-David F, Bouzeghrane F, Couture P, Thibault G. Thy-1 expression by cardiac fibroblasts: Lack of association with myofibroblast contractile markers. J Mol Cell Cardiol. 2007; 42:991-1000
24. Seubert J M, Sinal C J, Graves J, DeGraff L M, Bradbury J A, Lee C R, Goralski K, Carey M A, Luria A, Newman J W, Hammock B D, Falck J R, Roberts H, Rockman H A, Murphy E, Zeldin D C. Role of soluble epoxide hydrolase in postischemic recovery of heart contractile function. Circ Res. 2006; 99:442-450
25. Lee A S, Wu J C. Imaging of embryonic stem cell migration in vivo. Methods Mol Biol. 2011; 750:101-114
26. Lian X, Hsiao C, Wilson G, Zhu K, Hazeltine L B, Azarin S M, Raval K K, Zhang J, Kamp T J, Palecek S P. Robust cardiomyocyte differentiation from human pluripotent stem cells via temporal modulation of canonical wnt signaling. Proc Natl Acad Sci USA. 2012; 109: E1848-1857
27. Singla D K, Hacker T A, Ma L, Douglas P S, Sullivan R, Lyons G E, Kamp T J. Transplantation of embryonic stem cells into the infarcted mouse heart: Formation of multiple cell types. J Mol Cell Cardiol. 2006; 40:195-200
28. Takimoto E, Champion H C, Li M, Belardi D, Ren S, Rodriguez E R, Bedj a D, Gabrielson K L, Wang Y, Kass D A. Chronic inhibition of cyclic GMP phosphodiesterase 5a prevents and reverses cardiac hypertrophy. Nat Med. 2005; 11:214-222
29. Esposito G, Rapacciuolo A, Naga Prasad S V, Takaoka H, Thomas S A, Koch W J, Rockman H A. Genetic alterations that inhibit in vivo pressure-overload hypertrophy prevent cardiac dysfunction despite increased wall stress. Circulation. 2002; 105:85-92
30. Zhang Z, He Y, Tuteja D, Xu D, Timofeyev V, Zhang Q, Glatter K A, Xu Y, Shin H S, Low R, Chiamvimonvat N. Functional roles of cav1.3 (a1d) calcium channels in atria: Insights gained from gene-targeted null mutant mice. Circulation. 2005; 112:1936-1944
31. Ripplinger C M, Li W, Hadley J, Chen J, Rothenberg F, Lombardi R, Wickline S A, Marian A J, Efimov I R. Enhanced transmural fiber rotation and connexin 43 heterogeneity are associated with an increased upper limit of vulnerability in a transgenic rabbit model of human hypertrophic cardiomyopathy. Circ Res. 2007; 101:1049-1057
32. Ripplinger C M, Lou Q, Li W, Hadley J, Efimov I R. Panoramic imaging reveals basic mechanisms of induction and termination of ventricular tachycardia in rabbit heart with chronic infarction: Implications for low-voltage cardioversion. Heart rhythm: the official journal of the Heart Rhythm Society. 2009; 6:87-97
33. Ambrosi C M, Ripplinger C M, Efimov I R, Fedorov V V. Termination of sustained atrial flutter and fibrillation using low-voltage multiple-shock therapy. Heart rhythm: the official journal of the Heart Rhythm Society. 2011; 8:101-108
34. Sirish P, Lopez J E, Li N, Wong A, Timofeyev V, Young J N, Majdi M, Li R A, Chen H S, Chiamvimonvat N. MicroRNA profiling predicts a variance in the proliferative potential of cardiac progenitor cells derived from neonatal and adult murine hearts. J Mol Cell Cardiol. 2012; 52:264-272
35. Goldsmith E C, Hoffman A, Morales M O, Potts J D, Price R L, McFadden A, Rice M, Borg T K. Organization of fibroblasts in the heart. Developmental dynamics: an official publication of the American Association of Anatomists. 2004; 230:787-794
36. Krenning G, Zeisberg E M, Kalluri R. The origin of fibroblasts and mechanism of cardiac fibrosis. J Cell Physiol. 2010; 225:631-637
37. Zeisberg E M, Kalluri R. Origins of cardiac fibroblasts. Circ Res. 2010; 107:1304-1312
38. Zeisberg E M, Tarnavski O, Zeisberg M, Dorfman A L, McMullen J R, Gustafsson E, Chandraker A, Yuan X, Pu W T, Roberts A B, Neilson E G, Sayegh M H, Izumo S, Kalluri R. Endothelial-to-mesenchymal transition contributes to cardiac fibrosis. Nat Med. 2007; 13:952-961
39. Souders C A, Bowers S L, Baudino T A. Cardiac fibroblast: The renaissance cell. Circ Res. 2009; 105: 1164-1176
40. Lopez J E, Myagmar B E, Swigart P M, Montgomery M D, Haynam S, Bigos M, Rodrigo M C, Simpson P C. {beta}-myosin heavy chain is induced by pressure overload in a minor subpopulation of smaller mouse cardiac myocytes. Circ Res. 2011; 109:629-638
41. Song H, Cha M J, Song B W, Kim I K, Chang W, Lim S, Choi E J, Ham O, Lee S Y, Chung N, Jang Y, Hwang K C. Reactive oxygen species inhibit adhesion of mesenchymal stem cells implanted into ischemic myocardium via interference of focal adhesion complex. Stem cells (Dayton, Ohio). 2010; 28:555-563
42. Levene H. Contributions to probability and statistics. In: Olkin I, ed. Essays in honor of harold hotelling. Stanford University Press; 1960:278-292.
43. Li Q, Guo Y, Ou Q, Chen N, Wu W J, Yuan F, O'Brien E, Wang T, Luo L, Hunt G N, Zhu X, Bolli R. Intracoronary administration of cardiac stem cells in mice: A new, improved technique for cell therapy in murine models. Basic Res Cardiol. 2011; 106:849-864.

It is understood that the examples and embodiments described herein are for illustrative purposes only and that various modifications or changes in light thereof are suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of increasing the survival, engraftment and/or integration of transplanted induced pluripotent stem cell-derived cardiomyocytes (hiPSC-CMs) into cardiac tissue of a subject in need thereof, comprising co-administering to the subject the hiPSC-CMs with an agent that increases the production and/or level of epoxygenated fatty acids, wherein the co-administration results in an increase in the survival, engraftment and/or integration of the transplanted hiPSC-CMs relative to administration of the hiPSC-CMs alone.

2. A method of reversing, mitigating and/or improving one or more symptoms associated with cardiomyopathy or cardiac arrhythmia in an subject in need thereof, said method comprising co-administering to said subject a population of induced pluripotent stem cell-derived cardiomyocytes (hiPSC-CMs) and an agent that increases the production and/or level of epoxygenated fatty acids.

3. The method of claim 1, wherein the subject has cardiomyopathy, and wherein the cardiomyopathy is one or more of hypertrophic cardiomyopathy, hypertensive cardiomyopathy, diabetic cardiomyopathy and dilated cardiomyopathy.

4. The method of claim 2, wherein said cardiomyopathy is due to or secondary to one or more of valvular heart disease, myocardial infarction, and familial hypertrophic cardiomyopathy, and wherein said valvular heart disease is secondary to rheumatic fever, myxomatous degeneration of the valve, or papillary muscle dysfunction.

5. The method of claim 2, wherein the cardiomyopathy is dilated cardiomyopathy, and wherein said dilated cardiomyopathy is one or more of alcohol-induced cardiomyopathy, viral-induced cardiomyopathy, idiopathic cardiomyopathy, familial dilated cardiomyopathy and dilated cardiomyopathy caused by administration of an anti-cancer drug or exposure to a toxic agent.

6. The method of claim 2, wherein the administration of said hiPSC-CMs and said agent or agents inhibits cardiac arrhythmia, wherein the cardiac arrhythmia is one or more of atrial fibrillation, atrial flutter, ventricular fibrillation and ventricular tachycardia.

7. The method of claim 1, wherein the agent comprises one or more epoxygenated fatty acids.

8. The method of claim 1, wherein the epoxygenated fatty acids are selected from the group consisting of cis-epoxyeicosatrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof.

9. A method of claim 1, wherein the agent is an inhibitor of soluble epoxide hydrolase ("sEH").

10. The method of claim 9, wherein the inhibitor of sEH comprises a primary pharmacophore selected from the group consisting of a urea, a carbamate, and an amide.

11. The method of claim 9, wherein the inhibitor of sEH comprises a phenyl ether or piperidine moiety attached to the pharmacophore.

12. The method of claim 9, wherein the inhibitor of sEH has an IC50 of less than about 100 μM.

13. The method of claim 1, wherein the subject is a human.

14. The method of claim 1, wherein the hiPSC-CMs are syngeneic, allogeneic or xenogeneic to the subject.

15. The method of claim 1, wherein the hiPSC-CMs are administered intravenously, intra-arterially or intralesionally.

16. The method of claim 1, wherein the hiPSC-CMs and the agent that increases the production and/or level of epoxygenated fatty acids are administered by different routes of administration.

17. The method of claim 9, wherein the hiPSC-CMs and the inhibitor of sEH are concurrently co-administered.

18. The method of claim 9, wherein the hiPSC-CMs and the inhibitor of sEH are sequentially co-administered.

19. The method of claim 1, wherein the hiPSC-CMs are syngeneic to the subject.

20. The method of claim 1, wherein the hiPSC-CMs are allogeneic to the subject.

21. The method of claim 1, wherein the hiPSC-CMs are xenogeneic to the subject.

* * * * *